(12) United States Patent
Dagdeviren et al.

(10) Patent No.: US 11,547,347 B2
(45) Date of Patent: Jan. 10, 2023

(54) FLEXIBLE PIEZOELECTRIC DEVICES FOR GASTROINTESTINAL MOTILITY SENSING

(71) Applicant: Massachusetts Institute of Technology, Cambridge, MA (US)

(72) Inventors: Canan Dagdeviren, Cambridge, MA (US); Carlo Giovanni Traverso, Newton, MA (US); Robert S. Langer, Newton, MA (US)

(73) Assignees: Massachusetts Institute of Technology, Cambridge, MA (US); The Brigham & Women's Hospital, Inc., Boston, MA (US)

( * ) Notice: Subject to any disclaimer, the term of this patent is extended or adjusted under 35 U.S.C. 154(b) by 760 days.

(21) Appl. No.: 16/152,785

(22) Filed: Oct. 5, 2018

(65) Prior Publication Data
US 2019/0104979 A1    Apr. 11, 2019

Related U.S. Application Data

(60) Provisional application No. 62/569,048, filed on Oct. 6, 2017.

(51) Int. Cl.
*A61B 5/00*    (2006.01)
*A61B 5/07*    (2006.01)
(Continued)

(52) U.S. Cl.
CPC ............ *A61B 5/42* (2013.01); *A61B 5/073* (2013.01); *A61B 5/1107* (2013.01); (Continued)

(58) Field of Classification Search
None
See application file for complete search history.

(56) References Cited

U.S. PATENT DOCUMENTS 4,844,076 A    7/1989    Lesho et al.
5,778,882 A *  7/1998    Raymond .............. A61B 5/002
                                                        600/513

(Continued)

FOREIGN PATENT DOCUMENTS

DE    29911803 U1    11/1999
WO    2008052136 A3  10/2008
(Continued)

OTHER PUBLICATIONS

Au-Yeung et al., Early clinical experience with networked system for promoting patient self-management. Am. J. Manag. Care 17, e277-e287 (2011). 11 pages.
(Continued)

*Primary Examiner* — Jacqueline Cheng
*Assistant Examiner* — Jairo H Portillo
(74) *Attorney, Agent, or Firm* — Smith Baluch LLP

(57) ABSTRACT

Improvements in ingestible electronics with the capacity to sense physiologic and pathophysiologic states have transformed the standard of care for patients. Yet despite advances in device development, significant risks associated with solid, non-flexible gastrointestinal transiting systems remain. Here, we disclose an ingestible, flexible piezoelectric device that senses mechanical deformation within the gastric cavity. We demonstrate the capabilities of the sensor in both in vitro and ex vivo simulated gastric models, quantified its key behaviors in the GI tract by using computational modeling, and validated its functionality in awake and ambulating swine. Our piezoelectric devices can safely sense mechanical variations and harvest mechanical energy inside the gastrointestinal tract for diagnosing and treating motility disorders and for monitoring ingestion in bariatric applications.

26 Claims, 23 Drawing Sheets
(19 of 23 Drawing Sheet(s) Filed in Color)

(51) Int. Cl.

| | | |
|---|---|---|
| *A61B 5/11* | (2006.01) | |
| *H01L 41/04* | (2006.01) | |
| *H01L 41/047* | (2006.01) | |
| *H01L 41/053* | (2006.01) | |
| *H01L 41/113* | (2006.01) | |
| *H01L 41/187* | (2006.01) | |
| *H01L 41/23* | (2013.01) | |
| *H01L 41/29* | (2013.01) | |
| *H01L 41/333* | (2013.01) | |
| *G01L 1/16* | (2006.01) | |
| *G01L 19/08* | (2006.01) | |
| *G01L 9/00* | (2006.01) | |

(52) U.S. Cl.
CPC .......... *A61B 5/1126* (2013.01); *A61B 5/4255* (2013.01); *A61B 5/6861* (2013.01); *A61B 5/6873* (2013.01); *H01L 41/042* (2013.01); *H01L 41/0477* (2013.01); *H01L 41/053* (2013.01); *H01L 41/1132* (2013.01); *H01L 41/1873* (2013.01); *H01L 41/1876* (2013.01); *H01L 41/23* (2013.01); *H01L 41/29* (2013.01); *H01L 41/333* (2013.01); *A61B 2560/0214* (2013.01); *A61B 2562/162* (2013.01); *A61B 2562/164* (2013.01); *G01L 1/16* (2013.01); *G01L 9/0022* (2013.01); *G01L 19/086* (2013.01)

(56) References Cited

U.S. PATENT DOCUMENTS

| | | | | |
|---|---|---|---|---|
| 2002/0198470 A1* | 12/2002 | Imran | ............... | A61B 5/036 600/587 |
| 2003/0212306 A1* | 11/2003 | Banik | ............... | A61F 2/0036 600/16 |
| 2004/0142014 A1* | 7/2004 | Litvack | ............... | A61K 38/28 424/423 |
| 2005/0065571 A1* | 3/2005 | Imran | ............... | A61N 1/36007 607/41 |
| 2007/0255334 A1* | 11/2007 | Keimel | ............... | A61N 1/36007 607/40 |
| 2008/0194912 A1* | 8/2008 | Trovato | ............... | A61B 1/00156 600/118 |
| 2008/0288013 A1* | 11/2008 | Schecter | ............... | A61N 1/368 607/23 |
| 2011/0034760 A1* | 2/2011 | Brynelsen | ............... | A61B 5/02055 600/37 |
| 2011/0034912 A1* | 2/2011 | de Graff | ............... | H01L 27/14632 606/41 |
| 2011/0077660 A1* | 3/2011 | Janik | ............... | A61N 1/0553 606/129 |
| 2012/0041270 A1* | 2/2012 | Williams | ............... | A61M 25/04 600/208 |
| 2012/0055257 A1 | 3/2012 | Shaw-Klein | | |
| 2012/0157804 A1* | 6/2012 | Rogers | ............... | H05K 1/0283 600/345 |
| 2013/0046150 A1* | 2/2013 | Devanaboyina | ..... | A61B 5/6823 600/382 |
| 2013/0090567 A1* | 4/2013 | Lee | ............... | A61B 5/742 600/529 |
| 2015/0057519 A1* | 2/2015 | Ben-David | ............... | A61B 5/6871 600/373 |
| 2016/0235569 A1* | 8/2016 | Diana | ............... | A61F 5/0063 |
| 2016/0356811 A1* | 12/2016 | Omidi | ............... | G01Q 70/18 |
| 2017/0194427 A1 | 7/2017 | Tian | | |
| 2018/0085605 A1* | 3/2018 | Maharbiz | ............... | A61B 5/686 |

FOREIGN PATENT DOCUMENTS

| | | |
|---|---|---|
| WO | 2011089128 A1 | 7/2011 |
| WO | 2011112229 A2 | 9/2011 |
| WO | 2015106282 A1 | 7/2015 |
| WO | 2016168789 A1 | 10/2016 |

OTHER PUBLICATIONS

Belknap et al., Feasibility of an ingestible sensor-based system for monitoring adherence to tuberculosis therapy. PLoS ONE 8, e53373 (2013).5 pages.

Bellinger et al., Oral, ultra-long-lasting drug delivery: Application toward malaria elimination goals. Science Translational Medicine 8, 365, (2016). 13 pages.

Beyerlein et al., Correlation between symptoms developed after the oral ingestion of 50 g lactose and results of hydrogen breath testing for lactose intolerance. Aliment. Pharmacol. Ther. 27, 659-665 (2008).

Bures et al., Small intestinal bacterial overgrowth syndrome. World J Gastroenterol 16, 2978-2990 (2010).

Cassilly et al., Gastric emptying of a non-digestible solid: assessment with simultaneous SmartPill pH and pressure capsule, antroduodenal manometry, gastric emptying scintigraphy. Neurogastroenterol Motil. 20, 311-319 (2008).

Dagdeviren et al., Conformable Amplified Lead Zirconate Titanate Sensors with Enhanced Piezoelectric Response for Cutaneous Pressure Monitoring. Nature Communications 5:4496, (2014). 10 pages.

Dagdeviren et al., Conformal piezoelectric energy harvesting and storage from motions of the heart, lung, and diaphragm. PNAS 111, 1927-1932 (2014). 6 pages.

Dagdeviren et al., Conformal Piezoelectric Systems for Clinical and Experimental Characterization of Soft Tissue Biomechanics. Nature Materials 14, 728-736, (2015). 11 pages.

Dagdeviren et al., Recent Progress in Flexible and Stretchable Piezoelectric Devices for Mechanical Energy Harvesting, Sensing and Actuation. Extreme Mechanics Letter 9(1), 9-281, (2016). 13 pages.

Dagdeviren et al., Transient, Biocompatible Electronics and Energy Harvesters Based on ZnO. Small 9 (20), 3398-3404, (2013). 7 pages.

Dagdeviren, The future of Bionic Dynamos. Science 354, 6316, 1109, (2016).

Famm et al., A jump-start for Electroceuticals. Nature 496, 160, (2013). 3 pages.

Iddan et al., Wireless capsule endoscopy. Nature 405, 417-417 (2000). 2 pages.

Jacobson et al., Preliminary communication: a pH endoradiosonde. Lancet. 15, 1224 (1957). 1 page.

Kim et al., Self-deployable current sources fabricated from edible materials. Journal of Materials Chemistry B 1, 31, 3781-3788 (2013). 9 pages.

Liao et al., Indications and Detection, Completion, and Retention Rates of Small-bowel Capsule Endoscopy: A Systematic Review. Gastrointestinal Endoscopy, 71, 2, (2010). 7 pages.

Merritt et al., The pressure curve fora rubber balloon. Am. J. Phys. 46, 976-977 (1978). 3 pages.

Mostafalu et al., Flexible and transparent gastric battery: Energy harvesting from gastric acid for endoscopy application. Biosensors and Bioelectronics 54, 292-296 (2014). 5 pages.

Nadeau et al., Prolonged energy harvesting for ingestible devices. Nature Biomedical Engineering 1, 0022 (2017). 8 pages.

Overvelde et al., Amplifying the response of soft actuators by harnessing snap-through instabilities. Proceedings of the National Academy of Sciences 112, 10863-10868 (2015). 6 pages.

Persano et al., Cooperativity in the enhanced piezoelectric response of polymer nanowires. Advanced Materials 00, 1-6, (2014). 7 pages.

Persano et al., High Performance, Flexible Piezoelectric Devices Based on Aligned Arrays of Nanofibers of Poly [(vinylidenefluoride-co-trifluoroethylene]. Nature Communications 4, 1633, (2013).10 pages.

(56) References Cited

OTHER PUBLICATIONS

Poeggel et al., Optical fibre pressure sensors in medical applications. Sensors 15, 17115-17148 (2015). 34 pages.
Sharpe et al., Strain Measurements of Silicon Dioxide Microspecimens by Digital Imaging Processing. Experimental Mechanics 47, 649-658, (2007). 10 pages.
Shi et al., An analytic model for skin modulus measurement via conformal piezoelectric systems. Journal of Applied Mechanics (ASME Transactions) 82, 091007, (2015). 7 pages.
Sirohi et al., Fundamental understanding of piezoelectric strain sensors. Journal of Intelligent Material Systems and Structures. 1;11(4):246-57, (2000).
Su et al., Microbridge Testing of Silicon Oxide/Silicon Nitride Layer Films Deposited on Silicon Wafers. Acta Materialia 48, 4901-4915, (2000). 15 pages.
Su et al., Splitting of neutral mechanical plane of conformal, multilayer piezoelectric mechanical energy harvester. Applied Physics Letter 107, 041905, (2015). 6pages.
Traverso et al., Physiologic status monitoring via the gastrointestinal tract. PLoS ONE 10, e0141666 (2015). 13 pages.
Yagnamurthy, Electromechanical behavior of PZT thin film composites for RF-MEMS. Masters Thesis, University of Illinois at Urbana Champaign, (2009). 62 pages.
Yang et al., Thermally resistant UV-curable epoxy-siloxane hybrid materials for light emitting diode (LED) encapsulation. J. Mater. Chem. 22, 8874-8880, (2012). 7 pages.
Yeo et al., Multifunctional epidermal electronics printed directly onto the skin. Adv. Mater. 25, 2773-2778 (2013). 6 pages.
Yong et al., A novel piezoelectric strain sensor for simultaneous damping and tracking control of a high-speed nanopositioner. IEEE/ASME Transactions on Mechatronics. 18(3):1113-21, (2013). 9 pages.
Yu et al., Chronically implanted pressure sensors: challenges and state of the field. Sensors 14, 20620-20644 (2014). 25 pages.
Dagdeviren et al., "Flexible piezoelectric devices for gastrointestinal motility sensing." Nature Biomedical Engineering 1.10 (2017): 807. 14 pages.
International Search Report and Written Opinion in International Patent Application No. PCT/US18/54523 dated Jan. 25, 2019, 19 pages.

\* cited by examiner

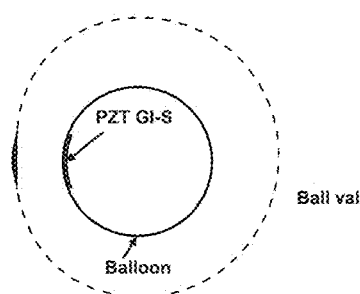
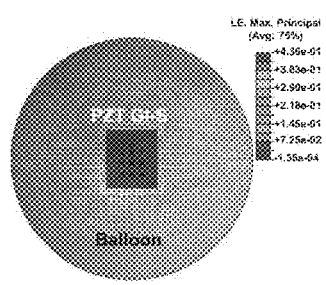
*FIG. 13A*  *FIG. 13B*
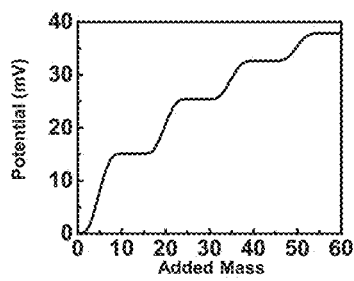
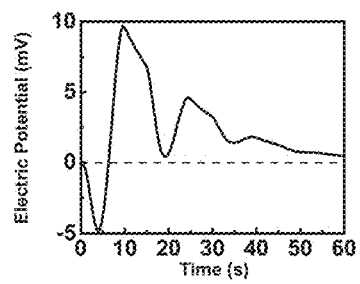
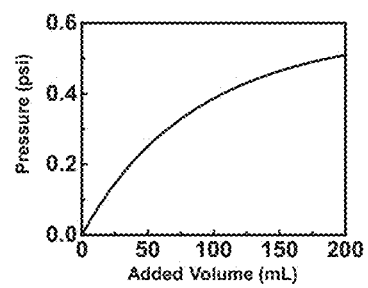
*FIG. 13C*  *FIG. 13D*  *FIG. 13E*

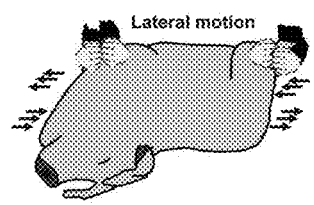 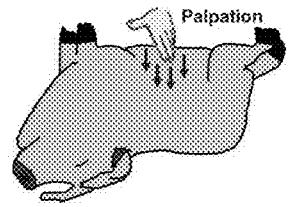
FIG. 19A    FIG. 19B
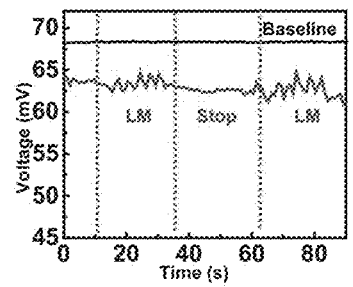 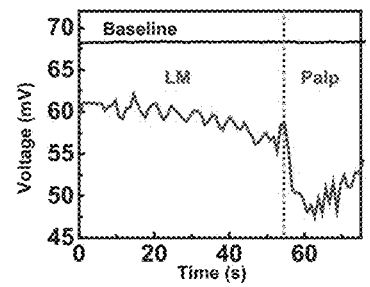
FIG. 19C    FIG. 19D
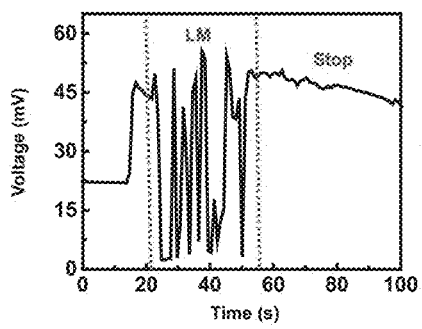 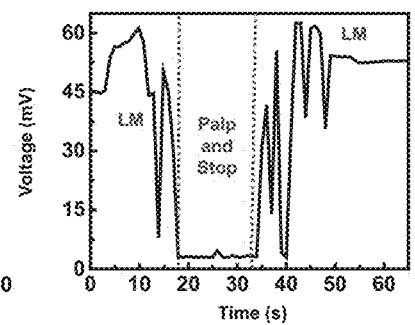
FIG. 19E    FIG. 19F

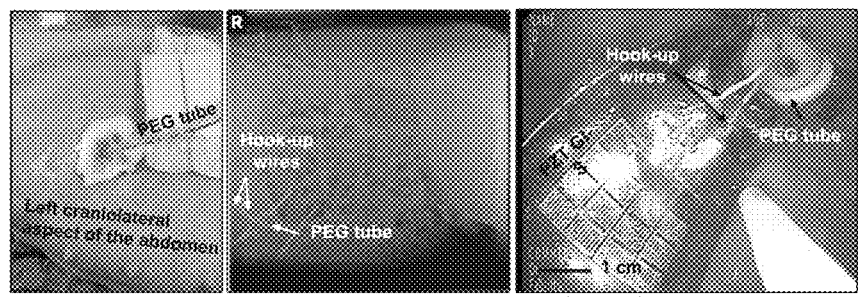
FIG. 20A      FIG. 20B      FIG. 20C
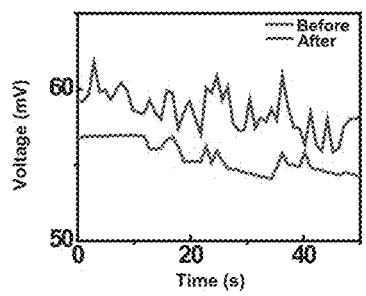 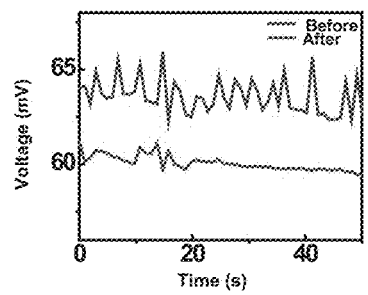
FIG. 20D      FIG. 20E
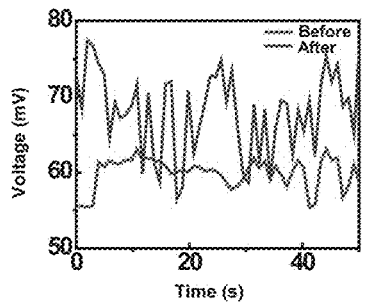 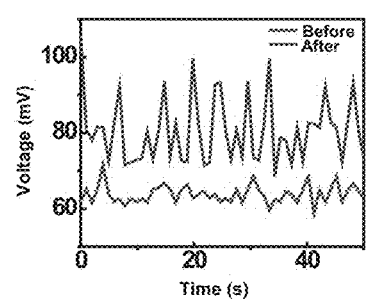
FIG. 20F      FIG. 20G

FLEXIBLE PIEZOELECTRIC DEVICES FOR GASTROINTESTINAL MOTILITY SENSING

CROSS-REFERENCE TO RELATED APPLICATION(S)

This application claims priority, under 35 U.S.C. § 119(e), to U.S. Application No. 62/569,048, filed on Oct. 6, 2017, and entitled "Flexible Piezoelectric Devices for Gastrointestinal Motility Sensing," which is entitled herein by reference in its entirety.

GOVERNMENT SUPPORT

This invention was made with Government support under Grant No. R37 EB000244 awarded by the National Institutes of Health. The Government has certain rights in the invention.

BACKGROUND

Systems for sensing of the gastrointestinal (GI) lumen have significantly extended the ability to diagnose and treat patients. Specifically, ingestible electronics have been developed to monitor pH, manometric pressure, temperature, dosage from ingestion to facilitate adherence monitoring and even vital signs, and for optical imaging in wireless endoscopy. Although these systems have had a significant impact on clinical practice, they are associated with complications including GI obstruction and limited battery lifespan, which may impact the completion rates of the evaluation.

SUMMARY

Recent progress in flexible electronics raises the potential for development of systems with the capability to both sense and remain flexible, allowing for deformation through the GI tract potentially mitigating GI obstruction. This advancement could reduce the risk for intestinal obstruction and extend current sensing capabilities by providing systems amenable to implantation for long term monitoring and/or stimulation. Particularly, active piezoelectric materials, which are more favorable than resistive materials due to their low power, high sensitivity, and easy readout, have fabrication techniques and associated device structures that expand the way electronic devices can be integrated within the body. Thus, ingestible flexible electronic devices offer an advanced platform to diagnose and treat motility disorders, monitor ingestion to aid in the treatment of obesity, and treat GI disorders in the form of GI electroceuticals.

Here, we disclose a flexible piezoelectric sensor system that can monitor vital signals and ingestion within the GI tract. The device is flexible enough to be folded into an ingestible, dissolvable capsule for delivery. As the capsule dissolves in GI fluid, the flexible sensor unfolds naturally and adheres to the gastrointestinal mucosa. The positioning of the device, therefore, allows monitoring of physiological states of the GI tract. Once implanted, the flexible sensor can remain in the GI tract for up to two days or more, where it senses ingestion and gastrointestinal motility to guide optimal therapeutic interventions. It may undergo thousands of cycles of bending and unbending in the acidic environment of the GI tract without cracking or suffering degraded electrical performance. It can power itself by harvesting energy from the GI motion.

Embodiments of this sensor technology include a device for sensing deformation of a gastrointestinal tract of a mammal, such as a person. This device comprises a flexible substrate, a piezoelectric element disposed on the flexible substrate, a polymer layer disposed on the piezoelectric element, and a biocompatible sealant disposed on the polymer layer and the piezoelectric element on the flexible substrate. In operation, the piezoelectric element, which may include a biocompatible piezoelectric material, produces an electrical signal in response to the deformation of the gastrointestinal tract of the mammal. The polymer layer insulates electrodes of the piezoelectric element. And the biocompatible sealant protects the piezoelectric element from acid in the gastrointestinal tract.

The flexible substrate can be folded and encapsulated in a dissolvable capsule and configured to unfold in response to the dissolvable capsule dissolving. And the dissolvable capsule can be endoscopically inserted within the gastrointestinal tract of the mammal.

The biocompatible sealant may comprise curable epoxy. It may have a thickness of about 100 nm to about 10 microns. And it may have a Young's modulus of about 0.01 GPa to about 5.0 GPa.

The device may also include a wireless transmitter, operably coupled to the piezoelectric element, to transmit the electrical signal to a receiver outside of the mammal. If so, the piezoelectric element can power the wireless transmitter with energy harvested from the gastrointestinal tract.

Another embodiment of the present technology includes a device for producing an electrical signal in response to expansion and/or contraction of a lumen wall of a gastrointestinal tract of a mammal. This device comprises at least one biocompatible piezoelectric element, a polymer encapsulating the biocompatible piezoelectric element, and a biocompatible sealant disposed on the polymer. In operation, the biocompatible piezoelectric element produces the electrical signal in response to the expansion and/or contraction of the lumen wall of the gastrointestinal tract of the mammal. The polymer insulates the biocompatible piezoelectric element's electrodes from each other, and the biocompatible sealant protects the piezoelectric element and the polymer from acid in the gastrointestinal tract. The entire device is folded and encapsulated in a dissolvable capsule and configured to unfold when the dissolvable capsule dissolves.

The biocompatible sealant can protect the polymer and the piezoelectric element from acid in the gastrointestinal tract for at least 48 hours. It can have a thickness of about 100 nm to about 10 microns and a Young's modulus of about 0.01 GPa to about 5.0 GPa. And the device can measure at least 10,000 expansions and/or contractions of the lumen wall.

Further embodiments of the present technology include methods of deploying and using flexible piezoelectric sensor systems in the GI tract. Such a method can include inserting a device (e.g., endoscopically) into the gastrointestinal tract of a mammal. This device can include a piezoelectric element disposed on a flexible substrate, which is folded and encapsulated in a dissolvable capsule. The dissolvable capsule is allowed to dissolve within the gastrointestinal tract so as to cause the flexible substrate to unfold within the gastrointestinal tract. The flexible substrate settles on a lumen wall of the gastrointestinal tract.

Once unfolded, the device can sense deformation of the lumen wall of the gastrointestinal tract with the device for about 12 hours to about 48 hours, for at least about 48 hours, for at least about 36 hours, for at least about 24 hours, and/or for at least about 12 hours. This may comprise sensing at least 10,000 expansions and/or contractions of the lumen wall of the gastrointestinal tract with the device.

Generally, sensing the deformation of the lumen wall comprises generating an electrical signal with the piezoelectric element. The device can wirelessly transmit a signal representing the deformation of the lumen wall to a receiver outside the mammal with a transmitter powered by the piezoelectric element. The signal may be used to determine that the mammal has ingested a fluid, such as air or a liquid, based on the deformation of the lumen wall.

Other inventive methods include sensing deformation (e.g., expansion and/or contraction) or filling of a lumen of a gastrointestinal tract of a mammal with a device disposed on the lumen wall. This device may include a flexible substrate, a piezoelectric element disposed on the flexible substrate, a layer of polymer disposed on the piezoelectric element, and a layer of sealant disposed on the layer of polymer.

Still other inventive methods include sensing, with a device disposed on a wall of a stomach of a mammal, ingestion of air or liquid by the mammal. This device can include a piezoelectric element disposed on the flexible substrate.

All combinations of the foregoing concepts and additional concepts discussed in greater detail below (provided such concepts are not mutually inconsistent) are part of the inventive subject matter disclosed herein. In particular, all combinations of claimed subject matter appearing at the end of this disclosure are part of the inventive subject matter disclosed herein. The terminology used herein that also may appear in any disclosure incorporated by reference should be accorded a meaning most consistent with the particular concepts disclosed herein.

BRIEF DESCRIPTIONS OF THE DRAWINGS

The patent or application file contains at least one drawing executed in color. Copies of this patent or patent application publication with color drawing(s) will be provided by the Office upon request and payment of the necessary fee.

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

Figure 6A:
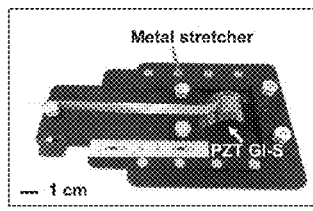
FIGS. 6A and 6B show a mechanical stretcher for bending/stretching a piezoelectric gastrointestinal sensor without (FIG. 6A) and with (FIG. 6B) stomach tissue.
Figure 6B:
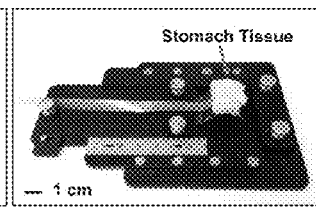
Figure 6C:
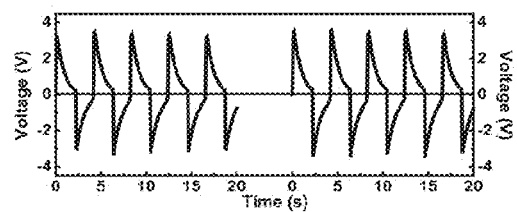
FIG. 6C is a plot of voltage output over time from repeated (10,000) bending cycles using the stretcher of FIGS. 6A and 6B without (left) and with (right) stomach tissue.
Figure 6D:
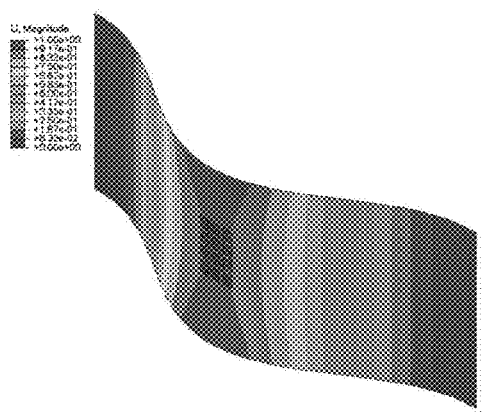
FIG. 6D shows the results of a finite element (FE) simulation of the piezoelectric gastrointestinal sensor.
Figure 6E:
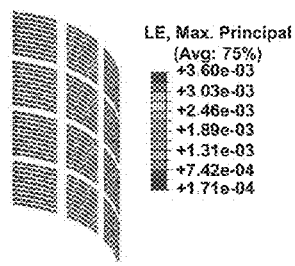

FIG. 6E shows the strain distribution in piezoelectric gastrointestinal sensor ribbon in bending. The maximum principal strain is much lower than the failure strain in the piezoelectric material. LE: Max. principle strain.

Figure 7:
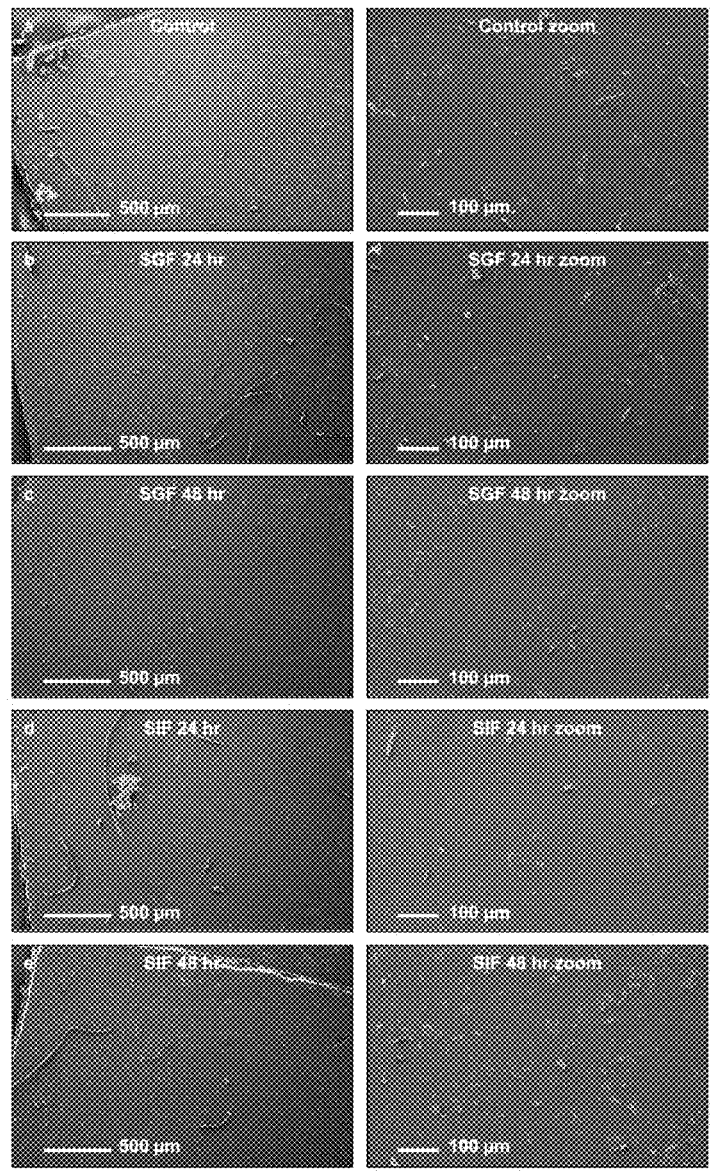

FIG. 7 shows scanning electron micrograph (SEM) images of piezoelectric gastrointestinal sensors over 48-hour immersions in simulated gastric fluid (SGF) and simulated intestinal fluid (SIF).

Figure 8:
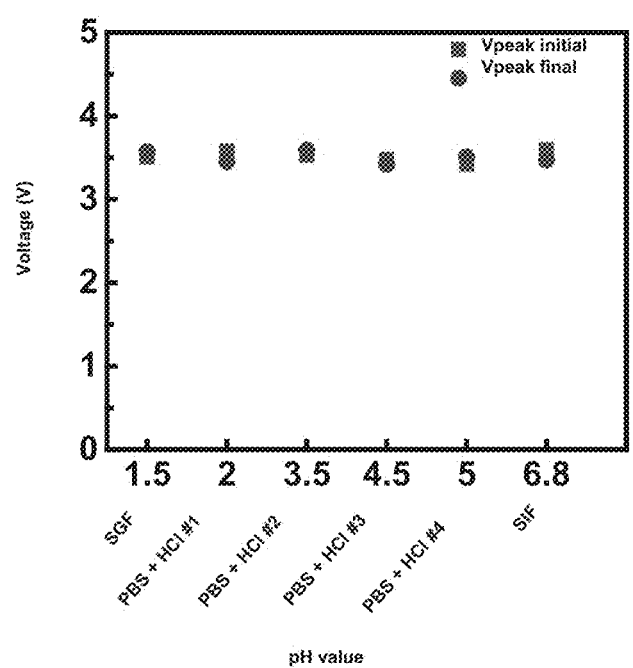

FIG. 8 is a plot showing the voltages produced by piezoelectric gastrointestinal sensor before (Vpeak initial) and after (Vpeak final) spending 48 hours undergoing repeated bending while immersed in solutions with different pH values.

Figure 9A:
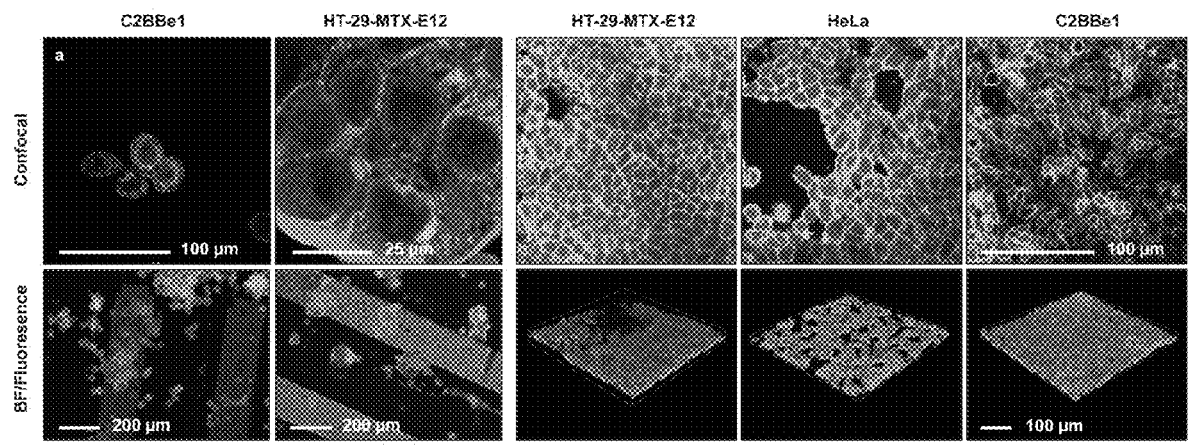

FIG. 9A shows high-resolution confocal microscopy images of HT-29-MTX-E12 and C2BBe1 cells grown on microchip device surface for three days followed by fixation and nucleus (Dapi, blue), F-actin (Phalloidin, green), and lysozyme (Lysomarker, red) staining.

Figure 9B:
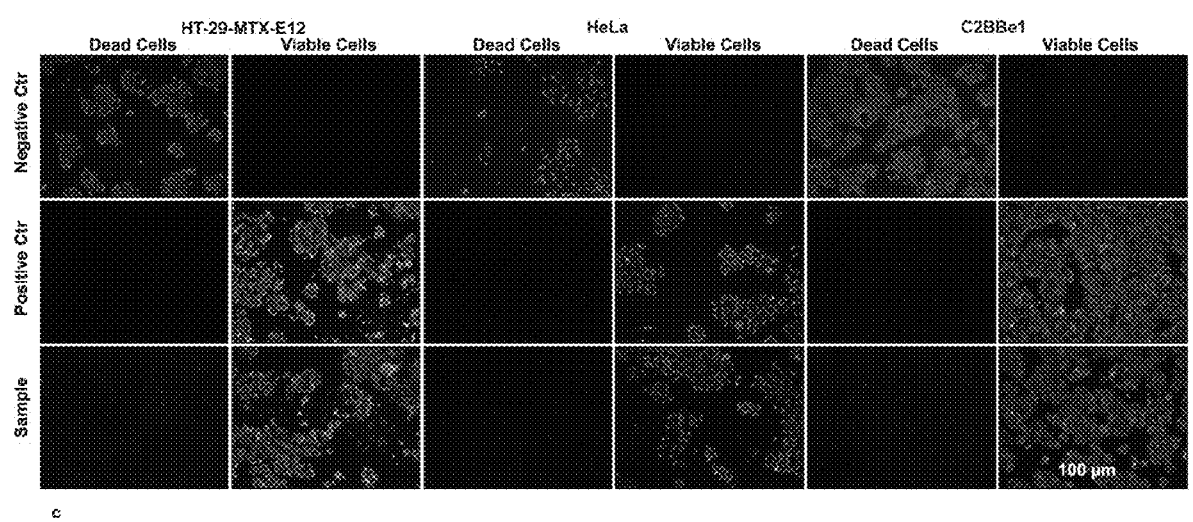

FIG. 9B shows a LiveDead cytotoxicity analysis of HT-29-MTX-E12, HeLa, C2BBe1 cells incubated with neutralized simulated gastric fluid for three days.

Figure 9C:
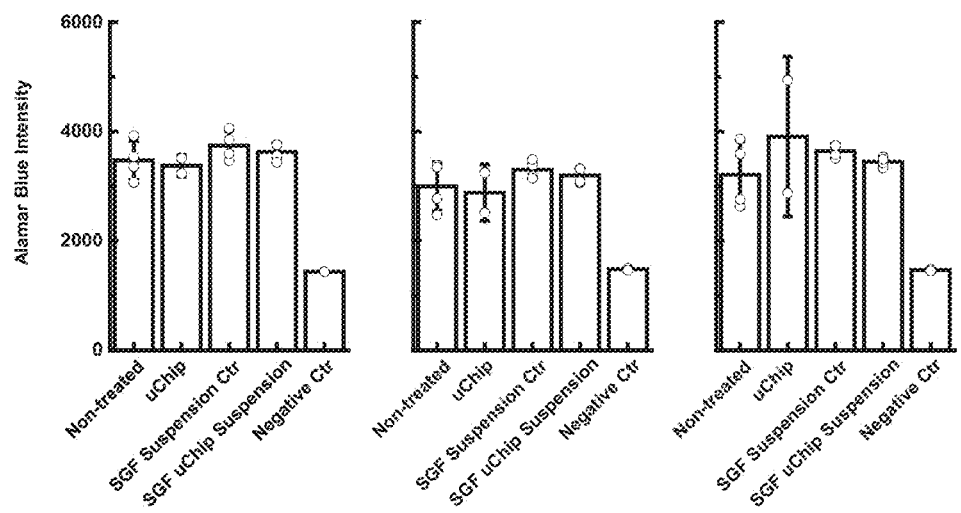

FIG. 9C shows bar graphs of AlamarBlue intensity of HT-29-MTX-E12 (left), HeLa (middle), and C2BBe1 (right) cells incubated with neutralized simulated gastric fluid for three days (SGF micro-chip suspension) or incubated with the micro-chip itself (micro-chip). The error bars are the standard deviation with center values as mean.

Figure 10A:
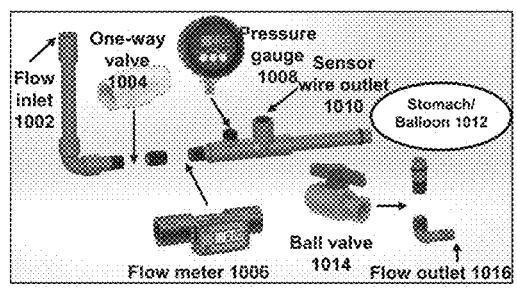

FIG. 10A is a schematic, exploded illustration an in vitro setup for simulating stomach behavior.

Figure 10C:
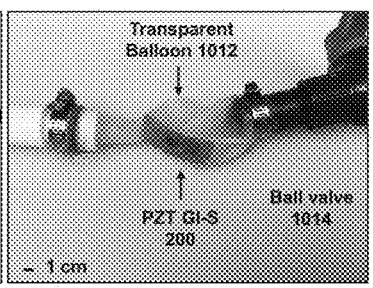
Figure 10B:
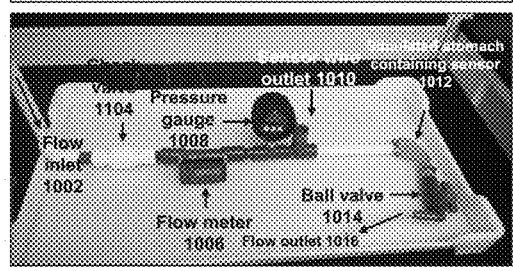

FIG. 10B is a photograph of the in vitro setup of FIG. 10A.

Figure 10D:
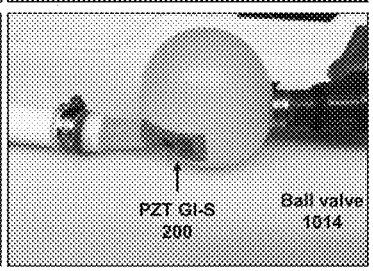

FIGS. 10C and 10D are photographs of the in vitro setup with a transparent balloon before (FIG. 10C) and after (FIG. 10D) 200 mL water infusion.

Figure 11A:
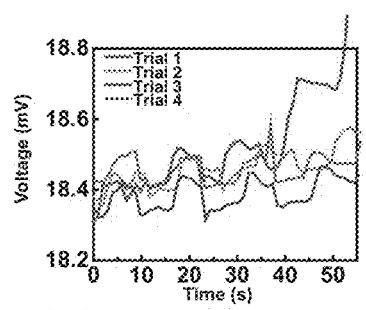

FIG. 11A is a plot of voltage versus time for a piezoelectric gastrointestinal sensor floating in a balloon with 200 mL of water infused in 50 mL increments.

Figure 11B:
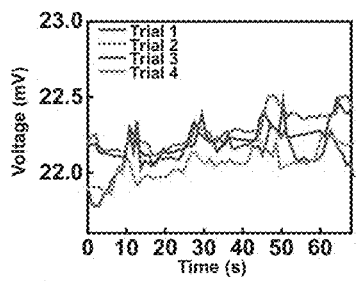

FIG. 11B is a plot of voltage versus time for a piezoelectric gastrointestinal sensor glued to an inner surface of a balloon with 200 mL of water infused in 50 mL increments.

Figure 11C:
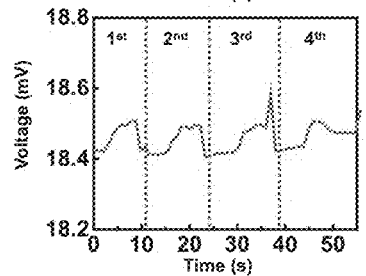

FIG. 11C a representative voltage output versus time graph for every 50 mL water infusion for the piezoelectric gastrointestinal sensor floating in the balloon.

Figure 11D:
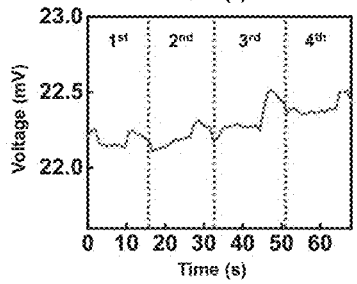

FIG. 11D a representative voltage output versus time graph for every 50 mL water infusion for the piezoelectric gastrointestinal sensor glued to the inner wall of the balloon.

Figure 11E:
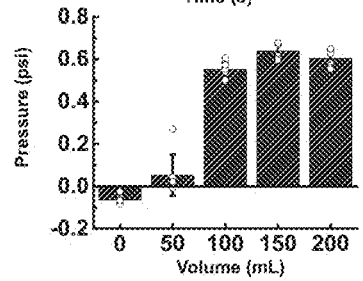

FIG. 11E shows average pressure variation during the water infusion in FIG. 11C for the floating piezoelectric gastrointestinal sensor. The error bars are the standard deviation with center values as mean.

Figure 11F:
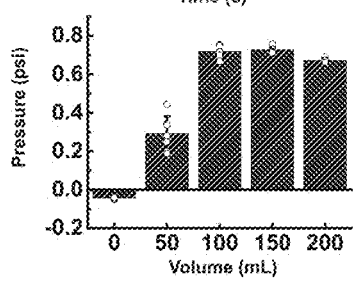

FIG. 11F shows average pressure variation during the water infusion in FIG. 11D for the glued piezoelectric gastrointestinal sensor. The error bars are the standard deviation with center values as mean.

Figure 12A:
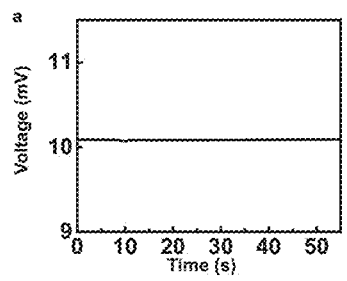

FIG. 12A is a plot of baseline voltage emitted by a floating piezoelectric gastrointestinal sensor in an in vitro measurement.

Figure 12B:
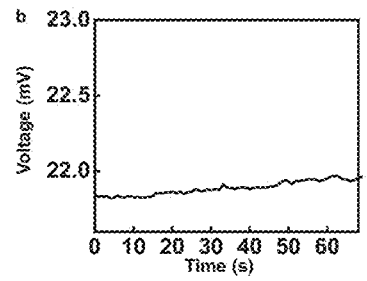

FIG. 12B is a plot of baseline voltage emitted by a secured piezoelectric gastrointestinal sensor in an in vitro measurement.

Figure 12C:
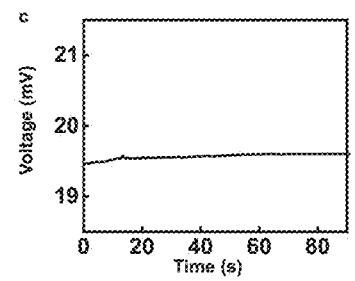

FIG. 12C is a plot of baseline voltage emitted by the piezoelectric gastrointestinal sensor floating in an ex vivo stomach measurement.

FIG. 13A shows undeformed (black solid line) and inflated (black dash line) stages of a finite element (FE) model of the piezoelectric gastrointestinal sensor attached to a hyper-elastic spherical balloon.

FIG. 13B shows strain distribution in the piezoelectric gastrointestinal sensor generated by infusing the balloon with 200 mL incompressible fluid as simulated with the FE model, LE: Max. principle strain.

FIG. 13C is a plot of electric potential generated with piezoelectric gastrointestinal sensor obtained from the FE model in an open circuit.

FIG. 13D is a plot of electric potential generated by the device obtained from an approximate analytical model.

FIG. 13E is a plot of simulated pressure generated in the balloon versus the water infused.

Figure 14A:
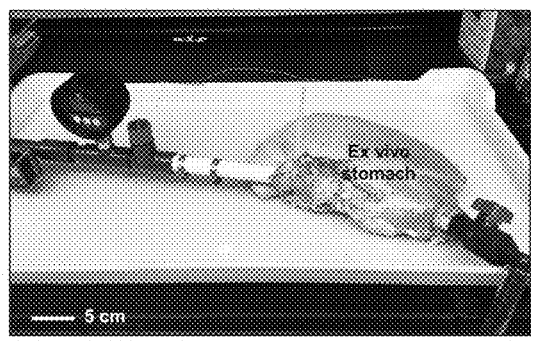
Figure 14B:
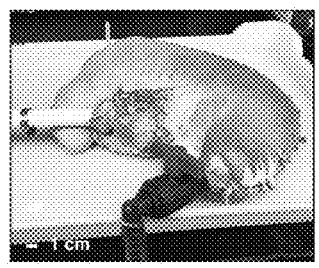

FIGS. 14A and 14B are photographs of an ex-vivo stomach integrated with in vitro set-up before (FIG. 14A) and after (FIG. 14B) 200 mL water infusion.

Figure 14C:
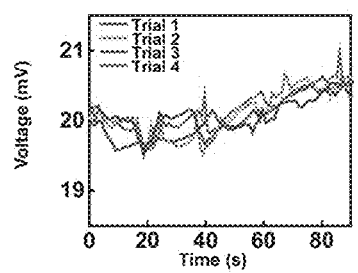

FIG. 14C is a voltage versus time graph for a piezoelectric gastrointestinal sensor in the ex vivo stomach with 200 mL water infused in 50 mL increments.

Figure 14D:
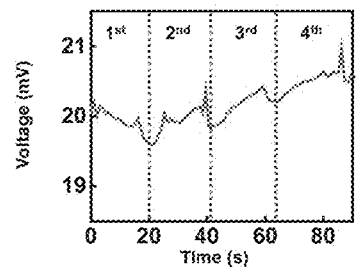

FIG. 14D is a representative voltage output versus time graph for every 50 mL water infusion for the piezoelectric gastrointestinal sensor in the ex vivo stomach.

Figure 14E:
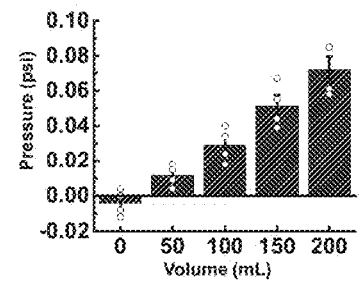

FIG. 14E is a graph of average pressure variation during the water infusion for the piezoelectric gastrointestinal sensor in the ex vivo stomach. The error bars are the standard deviation with center values as mean.

Figure 15:
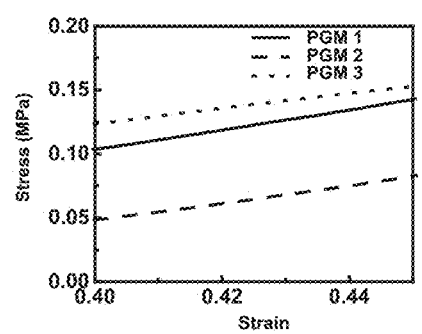

FIG. 15 is a truncated stress-strain curve for three different swine gastric mucosa samples (PGM 1, 2, and 3).

Figure 16A:
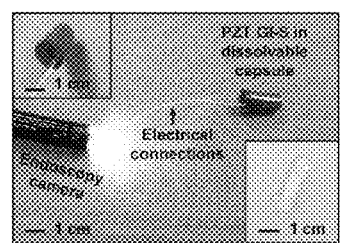

FIG. 16A is a photograph of piezoelectric gastrointestinal sensor before insertion into the stomach of a live pig. The top left inset shows the rolled piezoelectric gastrointestinal sensor in a dissolvable capsule (bottom right inset).

Figure 16B:
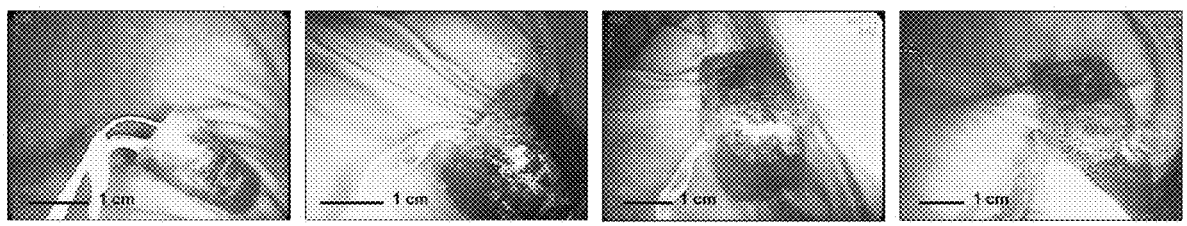

FIG. 16B is a series of photographs show the piezoelectric gastrointestinal sensor unfolding in the pig's stomach.

Figure 16C:
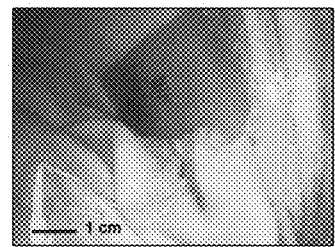

FIG. 16C is a photograph showing the piezoelectric gastrointestinal sensor in the pig's stomach.

Figures 17A, 17B:
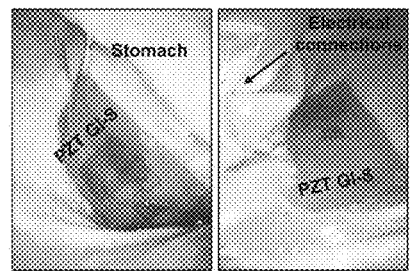

FIGS. 17A and 17B are photographs of a piezoelectric gastrointestinal sensor on the wall of stomach during inflation and deflation, respectively.

Figures 17C, 17D:
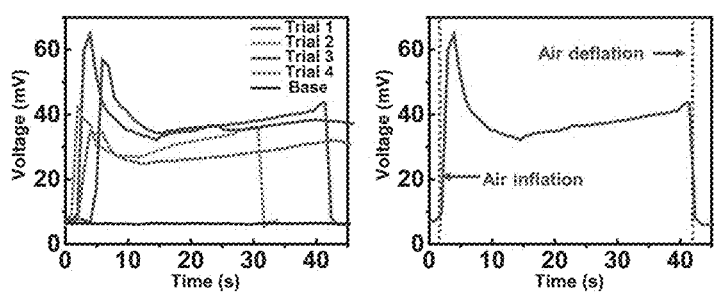

FIG. 17C is a plot of the corresponding voltage output from the inflation and deflation shown in FIGS. 17A and 17B.

FIG. 17D is a representative voltage output versus time graph of a cycle of inflation and deflation indicated by arrows.

Figures 18A, 18B:
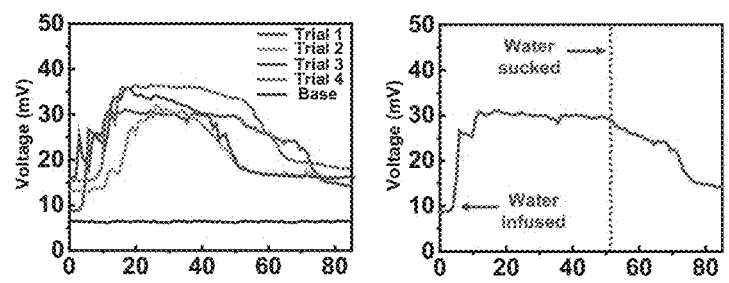

FIG. 18A shows voltage versus time for the piezoelectric gastrointestinal sensor in the swine stomach during 200 mL water infusion in 50 mL increments.

FIG. 18B is a plot of representative voltage output versus time of a cycle of water infusion and suction indicated in the arrows.

FIG. 19A is an illustration of lateral motion (LM) on the swine to mimic animal walking movements.

FIG. 19B is an illustration of abdominal palpation (palp) on the stomach of the swine to mimic the stomach movement.

FIG. 19C shows the output voltage generated by the piezoelectric gastrointestinal sensor from the LM-resting cycles in FIG. 19A with an absolute displacement value of 10 cm.

FIG. 19D shows the output voltage generated by the piezoelectric gastrointestinal sensor from the LM-palp cycles in FIG. 19B.

FIG. 19E is another plot of the output voltage generated by the piezoelectric gastrointestinal sensor from the LM-resting cycles in FIG. 19A.

FIG. 19F is another plot of the output voltage generated by the piezoelectric gastrointestinal sensor from the LM-palp cycles in FIG. 19B.

FIG. 20A is a photograph of a piezoelectric gastrointestinal sensor placed on the left craniolateral aspect of the swine abdomen via 20 French percutaneous endoscopic gastrostomy (PEG) tube. Using endoscopic guidance and an overtube, the piezoelectric gastrointestinal sensor attached to electronic connection wires was passed into the stomach and the wires were externalized through the PEG tube.

FIG. 20B is an X-ray image of the piezoelectric gastrointestinal sensor in the stomach of the swine taken after three days.

FIG. 20C is a photograph of the piezoelectric gastrointestinal sensor with the PEG tube inside the stomach.

FIG. 20D shows the voltage output by the piezoelectric gastrointestinal sensor for the morning trial of before and after milk ingestion during Day #1 of the in vivo test.

FIG. 20E shows the voltage output by the piezoelectric gastrointestinal sensor for the afternoon trial of before and after milk ingestion during Day #1 of the in vivo test.

FIG. 20F shows the voltage output by the piezoelectric gastrointestinal sensor for the morning trial of before and after milk ingestion during Day #2 of the in vivo test.

FIG. 20G shows the voltage output by the piezoelectric gastrointestinal sensor for the afternoon trial of before and after milk ingestion during Day #2 of the in vivo test.

DETAILED DESCRIPTION

The piezoelectric gastrointestinal sensors disclosed here can monitor vital signs and associated mechanical deformations of the gastric cavity. They can be used to diagnose and treat motility disorders and monitor ingestion for treating and evaluating obesity. The small dimensions and flexibility of these devices could reduce the likelihood of GI tissue damage, and thereby increase the devices' broad applicability. Furthermore, the device's flexibility allows for robust contact with soft tissues inside the stomach during gastric motion and enables compact packaging of the device within a dissolvable capsule facilitating oral delivery. In vivo pre-clinical measurements and measurements on ex vivo organs integrated with an in vitro setup show consistent performance in GI tract/cavity and corroborate the sensors' practical functionality. An example device can incorporate a wireless network, bioresorbable material components, multi-layer configurations to realize capabilities in transient and remotely controlled GI sensors, and/or mechanical energy harvesters.

Piezoelectric Gastrointestinal Sensors

Figure 1A:
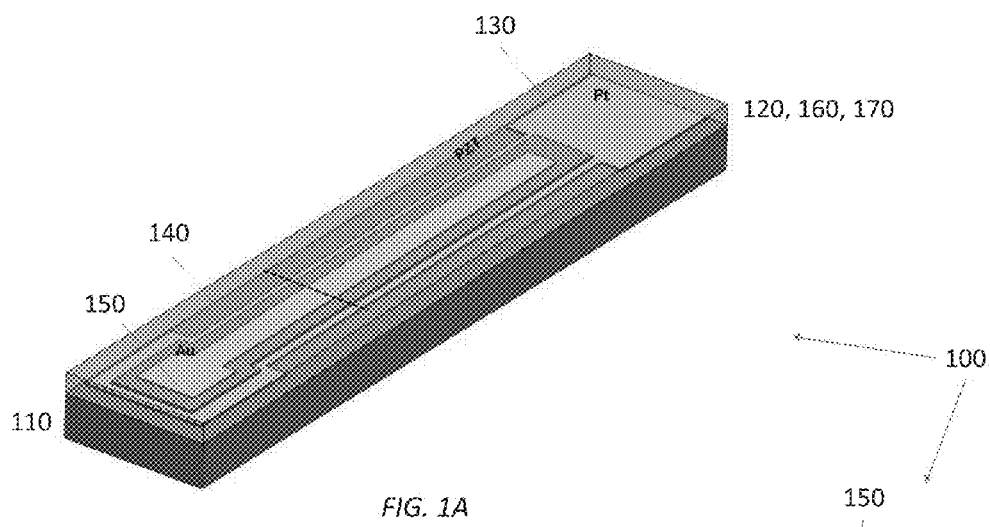
FIG. 1A is a perspective illustration of a piezoelectric gastrointestinal sensor with a single sensing element (ribbon) coated with a sealant (epoxy layer).
Figure 1B:
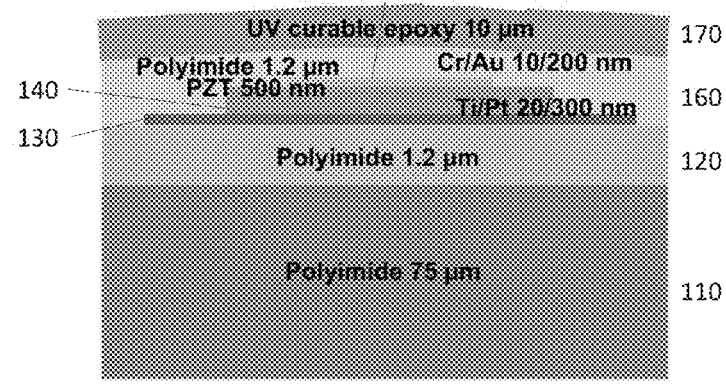
FIG. 1B is a cross-sectional view of the piezoelectric gastrointestinal sensor along the black dashed line in FIG. 1A.

FIGS. 1A and 1B show perspective and cross-sectional views of a piezoelectric gastrointestinal sensor 100. It includes a flexible substrate 110 (e.g., Kapton tape or a thick layer of polymer) coated with a first layer of biocompatible polymer 120 (e.g., a 1.2-micron polyimide (PI) layer). The GI-S 100 has a first electrode 130 (e.g., a 300 nm thick layer of Pt on a 20 nm thick layer of Ti) on the first polymer layer 120, which is precured and makes the other layers stick nicely to the flexible substrate 110.

A piezoelectric element 140, which may be made of piezoelectric material, such as a 500 nm thick layer of PZT or biocompatible KNM, extends over at least part of the first electrical contact 130. A second electrode 150 (e.g., a 200 nm thick layer of Au on a 10 nm thick layer of Cr) extends over at least part of the piezoelectric element 140. A second layer 160 of biocompatible polymer, such as another 1.2-micron-thick polyimide layer 120, encapsulates the first electrode 130, piezoelectric element 140, and second electrode 150. The second polymer layer 160 electrically isolates the electrodes from each other. Otherwise, the first electrode 130 could touch the second electrode 150, creating a short.

A sealant 170, such as UV-cured epoxy, encapsulates everything except the bottom of flexible substrate 110, which sits on the lining of the gastrointestinal lumen (e.g., the stomach lining) when the device is deployed. The sealant 170 has a thickness of about 100 nm to about 10 microns (e.g., 250 nm, 500 nm, 750 nm, 1 micron, 2.5 microns, 5 microns, 7.5 microns, or any other value between about 100 nm to about 10 microns). The sealant 170 may be very uniform, with few to no pinholes. It is flexible enough to bend many times (e.g., 5,000 times; 10,000 times; 15,000 times; or more) without cracking or delaminating. To quantify this flexibility, the sealant 170 may have a Young's modulus of about 0.01 GPa to about 5.0 GPa (e.g., 0.1 GPa, 0.25 GPa, 0.5 GPa, 0.75 GPa, 1.0 GPa, 2.0 GPa, 3.0 GPa, 4.0 GPa, or any other value between about 0.01 GPa and about 5.0 GPa).

In operation, the sealant 170 provides mechanical and electrical robustness in acidic environments (e.g., with pH values of ranging from 4-7 and possibly as low as 1.5 to 2), like the stomach, and adheres well to the polymeric substrate 110, preventing delamination. In particular, the sealant isolates the electrodes 130 and 150 and other conductive traces from fluids, including air and the contents of GI tract. The robustness of the sealant 170 enables the GI-S 100 to operate in the GI tract for 12 hours, 24 hours, 36 hours, 48 hours, or more.

UV-curable epoxy is an especially suitable sealant 170 due to its high bond strength. This epoxy is non-corrosive silicone with high bond strength and ideal for high speed adhesion and sealing applications. Other possible sealants include silicon oxide ($SiO_x$) thin films, pinhole-free and stress releasing poly-para-xylylene (parylene-C) thin films, and polymers and dielectric layers (e.g., $Al_2O_3/SiO_2/Al_2O_3$) formed with atomic layer deposition.

If desired, the electrodes 130 and 150 can be connected to electronic components via leads (not shown) that are completely or partially encapsulated by the polymer layers 120 and 160 and sealant 170. These electronic components may include a wireless transmitter or transceiver, power supply, and signal processing circuitry (e.g., a processor) electrically connected to the first electrode 130 and second electrode 150. These components may be encapsulated within or between the polymer layers 120 and 160 and sealed on the substrate 110 by the sealant 170. The wireless transmitter or transceiver can be operably coupled to the power supply and signal processing circuitry, which may also be operably coupled to each other and to the piezoelectric element 140 via the first electrode 130 and second electrode 150. If desired, the power supply, which can include a battery or capacitor, may regulate and store energy harvested by the piezoelectric element 140 through peristaltic motion of the gastrointestinal tract.

Piezoelectric Gastrointestinal Sensors with Multiple Piezoelectric Elements

The piezoelectric gastrointestinal sensor 100 in FIGS. 1A and 1B includes a single piezoelectric element 140. Other piezoelectric gastrointestinal sensors may include more than one piezoelectric element. The number, size(s), shape(s), and orientation(s) of these piezoelectric elements can be selected based on the measurements that the sensor is supposed to make. If each piezoelectric element produces a known voltage or current in response to motion of the gastrointestinal tract, then the number of piezoelectric elements can be selected based on the desired "gain": a sensor with more piezoelectric elements will produce a higher voltage or current than a sensor with fewer piezoelectric elements in response to the same motion. Thus, a sensor for smaller patients or patients with a smaller range of peristaltic motion may have more piezoelectric elements than a sensor for a larger patient.

Figure 2A:
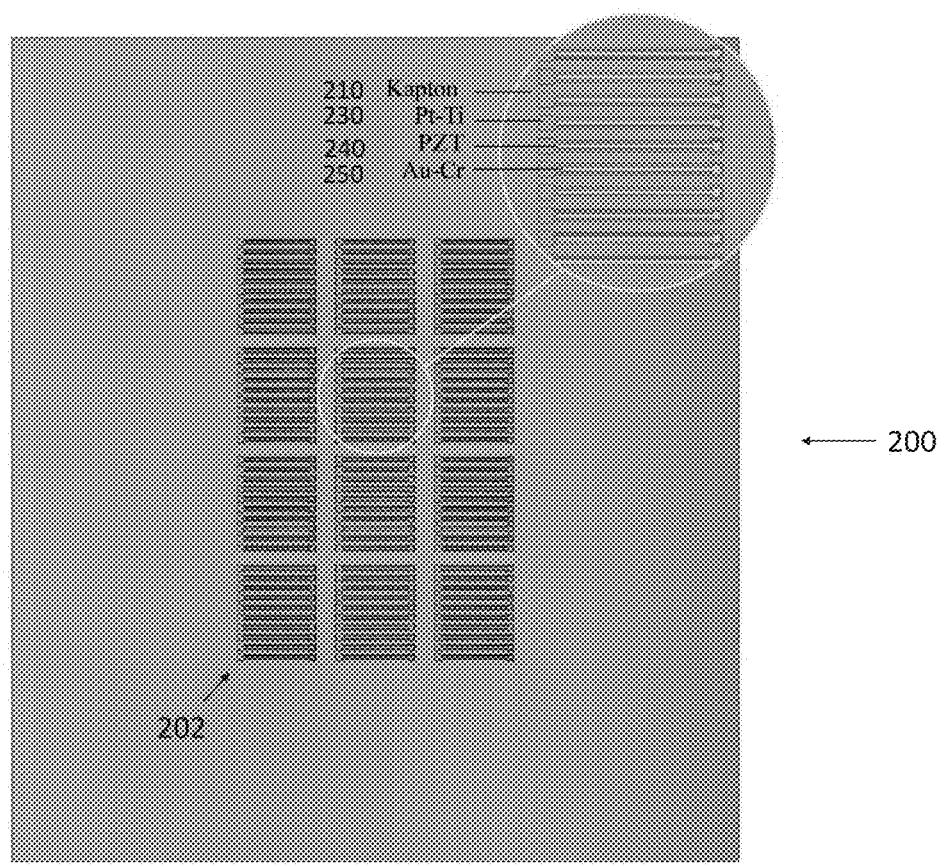
FIG. 2A shows a piezoelectric gastrointestinal sensor with several sensing elements (ribbon).
Figure 2B:
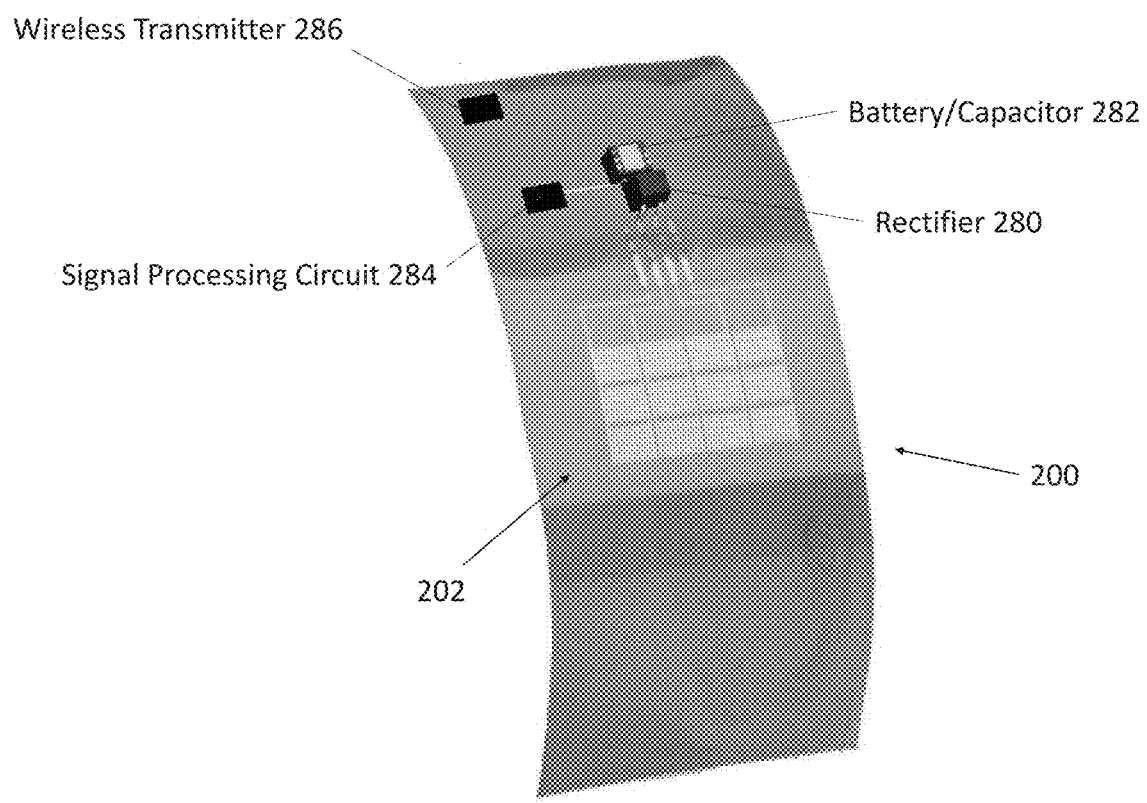
FIG. 2B shows the multi-ribbon piezoelectric gastrointestinal sensor with embedded electronic components.

FIGS. 2A and 2B show a piezoelectric gastrointestinal sensor 200 with many piezoelectric "ribbons" 202 for sensing movement of a lumen in the gastrointestinal tract. The inset at upper left shows a close-up of one group of ribbons 202. Each ribbon 202 includes a (biocompatible) piezoelectric layer 240 sandwiched between a pair of electrodes 230 and 250, just like the sensor 100 shown in FIGS. 1A and 1B. The ribbons 202 are encapsulated in biocompatible polymer (e.g., PI), which in turn is sealed with a flexible sealant (e.g., UV-cured epoxy) as shown in FIG. 1B.

In this sensor 200, includes twelve groups of ten ribbons 202 arranged in a 4×3 array with all of the ribbons 202 parallel to each other. The twelve groups of PZT ribbons connected in series, and the ribbons in each group are connected in parallel. In other sensors, there may be more or fewer ribbons, and the ribbons can be arranged in different arrangement, such as in a checkerboard pattern or other pattern with ribbons oriented in orthogonal directions to sense motion in different directions. For example, the ribbons 202 may be relatively long (e.g., 5 mm, 10 mm, 15 mm, 20 mm, 25 mm, 3 cm, 4 cm, 5 cm, 6 cm, or longer) and be arranged to traverse different compartments of the GI tract, including the esophagus and stomach or the stomach and duodenum.

FIG. 2B shows electronic components coupled to the ribbons 202. These components can be encapsulated by the sealant layer 170 (FIG. 1B) for protection from gastric juices and may include a rectifier 280 that converts alternating current (AC) generated by the ribbons 202 in response to GI motion into direct current (DC). The direct current can be used to charge a power supply 282, such as a battery or capacitor, that is coupled to the rectifier 280 and supplies power to a signal processing circuit 284 and a wireless transmitter 286. Put differently, the ribbons 202 and rectifier 280 harvest energy from the GI tract and store that energy in the power supply 282.

The ribbons 202 also supply analog signals to the signal processing circuit 284, which may include an analog-to-digital converter that converts the analog signals into digital signals. The signal processing circuit 284 may include digital logic for processing the digital signals and a memory or buffer for storing representations of the raw and/or processed digital signals. The signal processing circuit 284 transmits these representations to the wireless transmitter 286, which transmits them to a receiver on or outside the patient. The wireless transmitter 286 may transmit these signals continuously for continuous monitoring (e.g., during a device implantation, surgical procedure, or test), periodically (e.g., every hour or six hours to reduce energy consumption), or in response to a trigger (e.g., a trigger signal from the receiver, detected motion, full or nearly full memory, or threshold power supply level). The signal processing circuit 284 and wireless transmitter 286 may also broadcast information about the sensor's status, including its battery state and operating mode.

Making Piezoelectric Gastrointestinal Sensors

Figure 3:
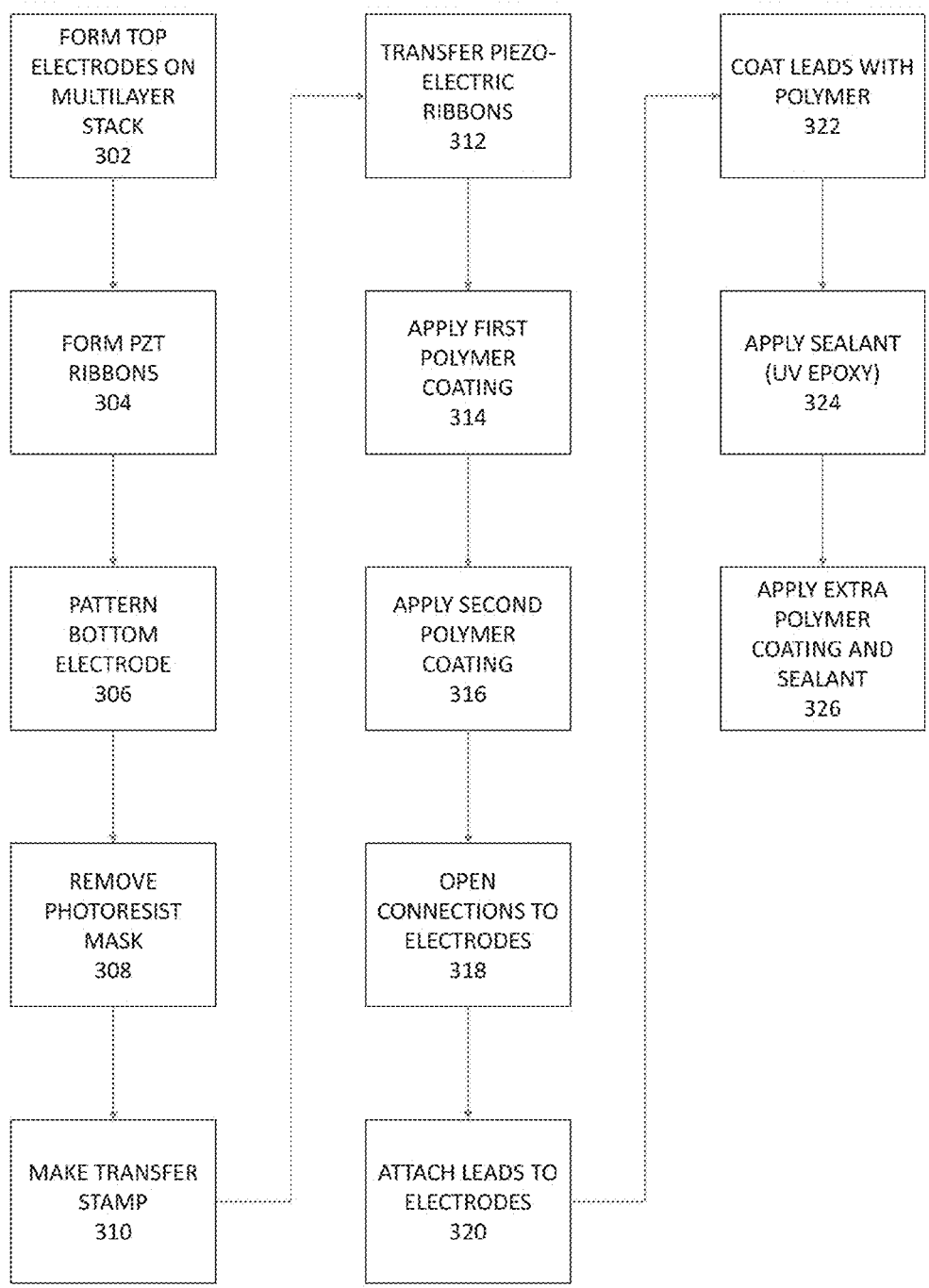
FIG. 3 is a flowchart that shows how to make a piezoelectric gastrointestinal sensor.

FIG. 3 is a flowchart that illustrates a process 300 for making a piezoelectric gastrointestinal sensor like the ones shown in FIGS. 1A, 1B, and 2. Briefly, the top electrode of the PZT ribbons are formed by deposition of Au/Cr (200 nm/10 nm) with an electron beam evaporator and associated photolithography steps on the surface of a multilayer stack of $Pb(Zr_{0.52}Ti_{0.48})O_3/Pt/Ti/SiO_2$ (500 nm/300 nm/20 nm/600 nm; INOSTEK) on a silicon (Si) wafer (step 302). Piezoelectric lead zirconate titanate (PZT) ribbons with thickness of 500 nm are created by wet chemical etching with $HNO_3$ (nitric acid):BHF (buffered hydrogen fluoride): $H_2O$ (DI water)=4.51:4.55:90.95 through a hard-baked mask of photoresist (PR) (step 304).

Later, the bottom Pt/Ti electrode are patterned by wet chemical etching. The PZT layers are protected photolithographically by photoresist (PR) during partial removal of the sacrificial layer, $SiO_2$ with dilute HF (hydrofluoric acid) (DI water: 49% HF=1:3) (step 306). The hard-baked PR mask is completely removed in an acetone bath for 3 hours (step 308). A PDMS stamp for transfer is fabricated by a mixture of PDMS (Sylgard 184, Dow Corning; 10:1 ratio of prepolymer to curing agent) in a plastic petri dish and curing at room temperature for 24 hours (step 310).

Next, the stamp is conformally contacted on the top of the fabricated ribbons. The ribbons are retrieved by peeling the stamp away from the Si wafer and then transfer printed on a film of PI (75 μm, DuPont, USA) (step 312). This film is formed by spin-coating a layer of poly(pyromellitic dianhydride-co-4,4'-oxydianiline) amic acid solution, to a thickness of 1.2 μm (step 314). The printed PZT ribbons on the PI are spin-coated with another layer of PI for encapsulation and hard baked at 250° C. in a vacuum oven (step 316). Optionally, to open contact holes for the top and bottom electrodes, the top layer of PI is patterned and etched in reactive ion etching (RIE, March) (step 318). If desired, electrical connection lines can be obtained by the deposition of Au/Cr (200 nm/10 nm) using electron beam evaporation (optional step 320). The interconnection lines may be spin-coated with another layer of PI for encapsulation and hard baked at 250° C. in a vacuum oven (step 322). As a final encapsulation of the entire piezoelectric gastrointestinal sensor, a 10 μm thick layer of UV curable epoxy (LOCTITE 5055™, Henkel Corp) is coated on the device surface (step 324).

The piezoelectric gastrointestinal sensor module may be further encapsulated with a 1.2 μm thick layer of polyimide and a 10 μm thick of UV curable epoxy (LOCTITE 5055™, Henkel Corp) (step 326). The electrical connection between the module and the computer controllable USB multimeter can be created via polytetrafluoroethylene (PTFE) hook-up wires (Cu conductor, 30 AWG wire gauge, 0.006 PTFE insulation thickness, Alpha Wire). The output metal trace of piezoelectric gastrointestinal sensor module and hook-up wire can be soldered with lead free solder (Sn96 Ag3.0 Cu0.5, Kester) by a digital soldering station power (WD1, Weller®). The completed piezoelectric gastrointestinal sensor can be rolled or folded for endoscopic insertion and deployment in a patient's gastrointestinal tract as illustrated in FIGS. 4A-4F, described below.

Those of skill in the art will readily understand that the process 300 in FIG. 3 can be modified to use different materials (e.g., biocompatible KNM instead of PZT), different layer thickness (e.g., a 5-micron UV epoxy layer, etc.) without departing from the scope of the inventive technology. The steps in this process can also be combined and/or rearranged as appropriate. For more information on making piezoelectric sensors on flexible substrates, please see U.S. Pre-Grant Publication No. 2016/0346556 A1 to Slepian et al. or U.S. Pre-Grant Publication No. 2018/0103852 A1 to Dagdeviren et al., each of which is incorporated herein by reference in its entirety.

Folding a Piezoelectric Gastrointestinal Sensor for Deployment

FIGS. 4A-4F illustrate a process for rolling or folding a piezoelectric gastrointestinal sensor and coating it with or inserting it into a dissolvable gelatin capsule 402. Thanks to its flexible substrate and layers, a flat piezoelectric gastrointestinal sensor 400 (FIG. 4A) is rolled, wound, or folded into a more compact shape (FIGS. 4B-4D), e.g., like photographic film is rolled or wound before being placed in a cylindrical film capsule. The sensor 400 can be rolled, wound, folded, or bent without fear of bending, crimping, or creasing.

Figures 4A, 4B, 4C, 4D, 4E, 4F:
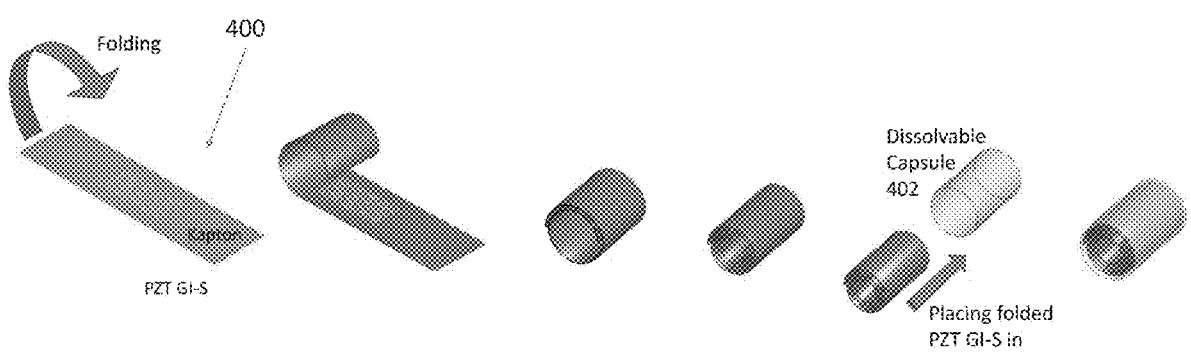
FIGS. 4A-4F illustrate a process for folding or rolling a piezoelectric gastrointestinal sensor for insertion in a dissolvable capsule.

In FIG. 4E, the rolled piezoelectric gastrointestinal sensor 400 is inserted into a cavity in a dissolvable capsule 402 made of gelatin or another dissolvable, biocompatible substance. Here, the cavity is defined by the capsule, which may have a diameter of about 1 cm and a length of about 2.7 cm. In general, non-surgical administration to the upper GI tract is limited by the esophagus, giving a maximum capsule diameter of about 1.5 cm, although the capsule can be longer (e.g., about 4 cm long to about 6 cm long) if the entire package is flexible enough. If ingested, the capsule should be no more than about 1 cm in diameter by about 3.3 cm in length. Once inserted into the dissolvable capsule, the rolled piezoelectric gastrointestinal sensor 400 (FIG. 4F) can be inserted into the stomach or other part of the gastrointestinal tract. The sensor 400 unfolds naturally as the capsule dissolves; it does not need to be biased to promote unfolding in a particular direction.

Using a Piezoelectric Gastrointestinal Sensor in the Gastrointestinal Tract

Once the piezoelectric gastrointestinal sensor has been encapsulated in gelatin or placed inside a gelatin capsule, it can be inserted into the gastrointestinal tract. It may be ingested, it which the size and composition of the capsule may be selected such that the capsule dissolves completely in the stomach or another part of the GI tract. It can also be inserted endoscopically and held in position until the capsule dissolves. In either case, the sensor unfolds as the capsule dissolves. It settles onto the wall of the GI lumen (e.g., the stomach wall), where electrostatic, surface tension, and/or Van der Waals force forces cause it to adhere. The sensor can also be affixed to a particular portion of the lumen wall, e.g., using a surgical adhesive or suture.

Once unfolded and in place, the sensor's piezoelectric element(s) generate electrical signals, such as a varying current or voltage, that represents the motion of the lumen wall. For instance, as the lumen expands and contracts, it may stretch and compress the sensor's piezoelectric elements, which produce voltage changes proportional to the amount of stretching and compressing. The sensor may store representations of these changes in an on-board memory. It can also transmit representations of these changes to a receiver outside the patient, such as a cell phone or computer, via an onboard wireless transmitter. A processor in or coupled to this external receiver may process and/or display the data from the sensor to a healthcare professional, who may use the information to diagnose or monitor the patient. In some cases, the processor may automatically identify certain events, such as ingestion of air or liquid, based on calibration data or certain signatures (e.g., spikes for air ingestion) in the data.

The sensor remains in place for as long as desired, e.g., 12 hours, 24 hours, 36 hours, 48 hours, or until it stops working or the study is over. The patient may pass the sensor out of the GI tract, or the sensor can be retrieved endoscopically.

Simulated and Experimental Results

Figure 5A:
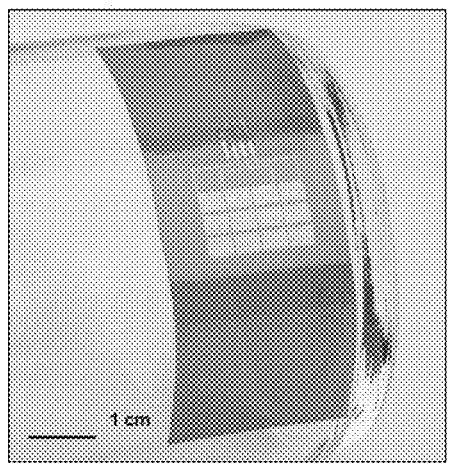
FIG. 5A is a photograph of a piezoelectric gastrointestinal sensor bent around a glass cylinder.
Figure 5B:
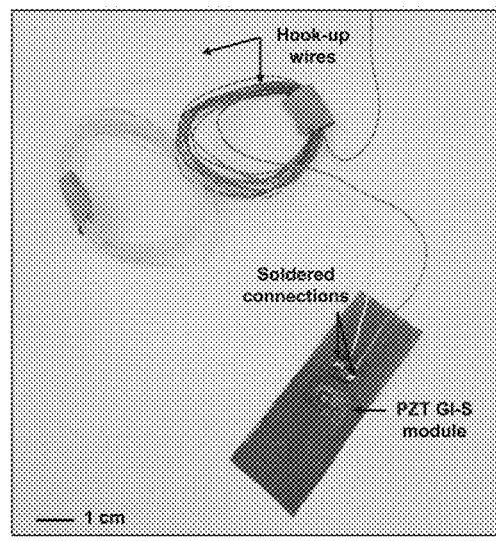
FIG. 5B shows a piezoelectric gastrointestinal sensor with attached electrical leads.
Figure 5C:
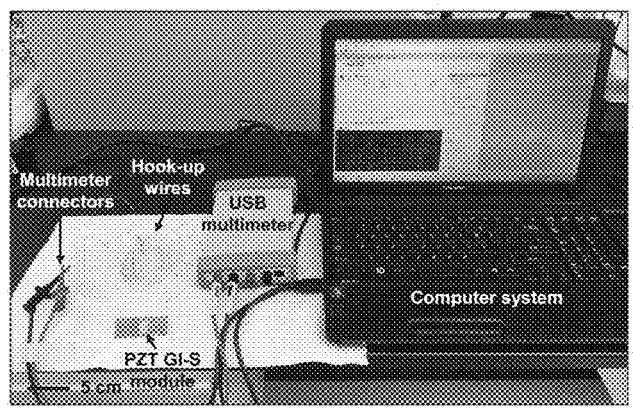
FIG. 5C shows a test set-up for benchtop measurements of a piezoelectric gastrointestinal sensor's mechanical and electrical properties.

FIGS. 5A-5C are photographs of a piezoelectric gastrointestinal sensor like the one in FIGS. 2A and 2B used for proof-of-concept measurements and modeling. Like the sensor 200 in FIGS. 2A and 2B, the piezoelectric gastrointestinal sensor in FIGS. 5A-5C is comprised of twelve groups of PZT ribbons connected in series, where each group includes ten PZT ribbons connected in parallel. The entire module is encapsulated with a 1.2 µm thick layer of poly(pyromellitic dianhydride-co-4,40-oxydianiline) amic acid solution (PI, Sigma-Aldrich) followed by 10 µm thick layer of UV curable epoxy (LOCTITE 5055™, Henkel Corp) to provide protection and isolation from the GI environment.

FIG. 5A shows the sensor wrapped around a glass cylinder. This demonstrates the piezoelectric gastrointestinal sensor's ability to conform to a curvilinear surface like those inside the gastrointestinal tract. FIG. 5B shows the sensor's PZT ribbons with electrical connections that are polytetrafluoroethylene (PTFE) hook-up wires (Copper conductor, 30 AWG wire gauge, 0.006 PTFE insulation thickness, Alpha Wire) with a length of two meters. In FIG. 5C, these wires are used to attain signal collections via a computer controllable USB multimeter (Keysight, U2741A) and a computer system.

Mechanical and Electrical Stability Measurements

FIGS. 6A-6E illustrate tests and simulations performed to study mechanical and electrical properties of a piezoelectric gastrointestinal sensor integrated to stomach tissue. FIGS. 6A and 6B shows a custom metal stretcher used to perform mechanical cycling tests. The stretcher bent the sensor without (FIG. 6A) and with (FIG. 6B) a 2 cm×2 cm piece of stomach tissue on top, leaving all tissue layers intact. FIG. 6C shows the voltage produced by the piezoelectric gastrointestinal sensor during the bending tests with (left) and without (right) the tissue. The bending results suggest that the piezoelectric gastrointestinal sensor is mechanically and electrically stable over 10K cycles.

FIG. 6D shows the results of a finite element (FE) simulation of the piezoelectric gastrointestinal sensor. The FE simulation revealed that piezoelectric gastrointestinal sensor buckles to a sinusoidal mode at a very low strain value of $\varepsilon=2.1\times10^{-5}$. Above this threshold, the device compensated for the applied compression via out-of-plane bending, as shown in FIG. 6E, with a maximum strain of $\varepsilon=4\times10^{-3}$ in the ribbons. Given that the bending strain is significantly lower than the failure strains of PZT and other materials, the cyclic loading does not lead to fatigue failure of the device.

Survivability in the Gastrointestinal Tract

FIG. 7 shows scanning electron micrograph (SEM, JEOL 5600LV, 5 kV, 20 spot size, HV, SEI) images of piezoelectric gastrointestinal sensors immersed in air (control), simulated gastric fluid (SGF), and simulated intestinal fluid (SIF) for 48 hours. Before visualization under SEM, all samples were sputter-coated with carbon using the Hummer 6.2 Sputter Coating System. Samples were cut to be under 0.5 cm² in area and fixed to the aluminum stubs by a double-sided adhesive carbon conductive tape.

The SEM images in FIG. 7 illustrate the sensor's ability to survive inside different parts of a person's gastrointestinal tract for 48 hours or more. The SEM images confirm that the sensor is mechanically stable over the course of 48 hours without any cracks and/or delamination of the encapsulation layer (sealant). This indicates that the sealant can protect the sensor's piezoelectric and electrical components from acid in a person's gastrointestinal tract for up to at least 48 hours.

FIG. 8 is a plot showing the voltages produced by piezoelectric gastrointestinal sensor before (Vpeak initial) and after (Vpeak final) spending 48 hours undergoing repeated bending while immersed in solutions with different pH values. These solutions were each 500 mL aliquots of ThermoFisher Scientific Phosphate-Buffered Saline (PBS), pH 7.4 were adjusted to pH values of 2, 3.5, and 5 via dropwise addition of Sigma-Aldrich Hydrochloric acid, ACS reagent, 37% (Sigma-Aldrich catalog #320331, CAS #7647-01-0). The pH values were measured using a Mettler Toledo InLab Expert Pro pH electrode combined with a Mettler Toledo pH/mV bench meter.

This pH test mimicked the change in pH of the gastric fluid depending on several factors, such as different GI disease conditions or diet. FIG. 8 shows no major voltage difference before and after 10,000 bending cycles and 48 hours of immersion. This shows that the sensor can stay electrically and mechanical stable for up to at least 48 hours in a person's gastrointestinal tract.

Cell Culture Study and Biocompatibility

We investigated the toxicity of the piezoelectric gastrointestinal sensor by cell cytotoxicity analysis of gastrointestinal model cells as recommended by the FDA Guidance of the International Standard (ISO 10993-1 Biological Evaluation of Medical Devices). This cell cytotoxicity analysis was performed based on the International Standard ISO-10993 (Biological Evaluation of Medical Devices) experimental guidelines. The cytotoxicity of the sensor in direct contact with cells as well as the cytotoxicity of released compounds in simulated gastric fluid (Sigma, 01651) was tested. Cells were seeded at a density of 20,000 cells/cm² a 48-well cell culture plate (Corning® Costar®, Sigma) containing the sterilized device or the sterilized release medium. The release medium consisted of simulated gastric fluid that was incubated with the device for 3 days at 37° C. Before being used for cytotoxicity analysis, the medium was neutralized using NaOH followed by sterile filtration. Cells were incubated for 3 days without exchanging the medium followed by AlamarBlue® Cell Viability assay (Cat. no. DAL1100, Lifetechnologies) as well as LIVE/DEAD® Viability/Cytotoxicity Kit, for mammalian cells (Cat. nb. L3224, Lifetechnologies) were performed for intact tissue explants according to manufacturer protocol using intestinal tissue treated with 70% (v/v) ETOH (ACS reagent, ≥99.5%, Sigma) in sterile filtered deionized water for 1 hour as negative control.

FIGS. 9A-9C illustrate results of the cell cytotoxicity analysis. FIG. 9A shows high-resolution confocal microscopy images of HT-29-MTX-E12 and C2BBe1 cells grown on piezoelectric gastrointestinal sensor surfaces for three days followed by fixation and nucleus (Dapi, blue), F-actin (Phalloidin, green), and lysozyme (Lysomarker, red) staining. These images were collected using an EVOS FL Cell Imaging System with 10× or 20× air objectives. Fluorescent samples were analyzed using a Nikon MR Ultra-Fast Spectral Scanning Confocal Microscope in a Galvano scanner using a 20× or 10× air objective. Resulting raw images were analyzed with NIS-Elements C software and ImageJ.

In FIG. 9A, the left panel shows fluorescence and brightfield overlap image of HT29-MTX and C2BBe1 cells grown on piezoelectric gastrointestinal sensor surfaces for three days followed by fixation and nucleus (Dapi, blue) and F-actin (Phalloidin, green) staining. The right side of FIG. 9A shows confocal microscopy images of HT-29-MTX-E12, HeLa, C2BBe1 cells grown on a microchip device surface for three days followed by fixation and staining for cell nucleus (Dapi, blue) and F-actin (Phalloidin, green). The images include representative confocal sections and a 3D reconstruction of a confocal stack.

FIG. 9B shows a LiveDead cytotoxicity analysis of HT-29-MTX-E12 (left), HeLa (middle), C2BBe1 (right) cells incubated with neutralized simulated gastric fluid for three days. Green indicates viable cells and red indicates dead cells. The scale bar shows 100 μm. The gastric fluid was used as a medium to incubate microchip devices for three days at 37° C. prior to neutralization and addition to cells. Cells treated with 70% EtOH were used as negative control, cells treated with neutralized gastric fluid that was not in contact with microchips were used as positive control.

FIG. 9C shows plots of AlamarBlue intensity of HT-29-MTX-E12 (left), HeLa (middle), C2BBe1 (right) cells incubated with neutralized simulated gastric fluid for three days (SGF micro-chip suspension) or incubated with the piezoelectric gastrointestinal sensor itself (micro-chip). Cells treated with 70% EtOH were used as negative control, cells treated with neutralized gastric fluid that was not in contact with microchips (SGF suspension control) or non-treated cells (non-treated) were used as positive controls. The error bars are the standard deviation with center values as mean.

FIGS. 9A and 9B show that gastrointestinal model cells co-incubated with the piezoelectric gastrointestinal sensor or exposed to compounds released from the sensor in simulated gastric fluid did not display cytotoxicity as assessed by measuring the cell metabolic activity as well as the plasma membrane integrity. The fluorescence and bright field microscopy overlap images in FIGS. 9A and 9B confirm that cells can adhere to the different materials in the sensor. Furthermore, high-resolution microscopical analysis of gastrointestinal model cells cultured on the surface of piezoelectric gastrointestinal sensor revealed cell adhesion and spreading on the device surface. Thus, the collective results support the potential for gastrointestinal tissue to grow around the device when implanted in the tissue (e.g., as shown by FIG. 9C).

In Vitro Assessment of Sensor Electrical Performance

We further confirmed the device functionality by in vitro experimental evaluations with a transparent balloon, connected to a flow inlet, a pressure gauge and a flow outlet to mimic the stomach. The in vitro evaluations included two cases: (I) the piezoelectric gastrointestinal sensor was free-floating inside the balloon and (II) the piezoelectric gastrointestinal sensor was affixed on the inner wall of the balloon with a thin layer (~10 μm) of Loctite Super Glue. In both cases, the piezoelectric gastrointestinal sensor was electrically connected to a USB multimeter to collect voltage outputs. Unless otherwise noted, the experiments were conducted with the PI substrate of GI-S in contact with the target substrate.

In Vitro Test Set Up

FIGS. 10A-10D illustrate the in vitro test set up. A one-foot length of standard ½" unthreaded PVC tubing was attached to ½" PVC coupling at the top and 90° PVC elbow at the bottom. Into the other end of the elbow, a ½" PVC thread-one-end pipe nipple was connected to form an inlet 1002. An NSF-certified PVC check valve 1004 was threaded onto PVC tubing to guarantee unidirectional flow. Threaded into the outflow end of the valve was a fully threaded ½" PVC pipe nipple. This was connected to a GPI TM Series water meter/totalizer 1006 which had an accuracy of ±3% FS and the ability to operate in a temperature range from 0° to 60° C. Another ½" PVC thread-one-end pipe nipple was used to connect the meter to a PVC tee fitting with a steel threaded inline reducer. Threaded into the top of the tee was an SSI Technologies MG1-5-A-9V-R pressure gauge 1008, which had an operating range of 0-5 PSI and −10° to 60° C. with an accuracy of ±1% FS. Into the first tee was the male end of a PVC tee with two female ends. An 8" length of standard ½" unthreaded PVC tubing was inserted into one female end. In the other, a rubber septum stopper from Chemglass was placed with a small hole (sensor wire outlet 1010) drilled into it for the wires of the device to exit the system. The wires were glued into place and made watertight using Loctite Super Glue Professional Liquid.

A clear 12" latex balloon 1012 was used as a stand-in for the stomach. In the experiments with the sensor 200 (FIGS. 2A and 2B) fixed to the balloon 1012, Loctite Super Glue Professional Liquid was used to adhere the sensor 200 to the inside of the balloon 1012. The mouth of the balloon 1012 was slid onto the end of the 8" PVC pipe over top of a two rubber 1/16" O-ring. A worm drive steel hose clamp was used to secure the balloon 1012 in place. A small hole was cut in the top of the balloon 1012 so the balloon 1012 could be secured to the unthreaded end of a ½" PVC thread-one-end pipe nipple in the same fashion as mentioned above. The nipple was threaded into a low-pressure PVC ball valve 1014 that could be opened to release fluids from the system. Fluids were administered to the test system at the top of the fluid inlet 1002 using a 60 mL Monojet oral medication syringe. This was pushed through a rubber septum stopper from Chemglass with a small hole drilled into it to form a seal. The unthreaded connections in the test system were sealed using plastic pipe cement for PVC. The threaded connections were sealed with commercial-grade pipe thread sealant tape.

FIGS. 10C and 10D show the balloon 1012 with the piezoelectric gastrointestinal sensor 200 in an uninflated state and inflated with water, respectively. The water infusion simulated fluid ingestion into the stomach. A total volume of 200 mL water at room temperature in 50 mL increments was infused into the balloon 1012 using a syringe. The rate of water infusion in the in vitro and ex vivo experiments was ~5 mL/s and 2.5 mL/s, respectively, and the duration of pauses between each 50 mL step of water insertion was 2 seconds.

FIGS. 11A and 11B show voltage outputs from the piezoelectric sensor when the balloon was empty (FIG. 10C) and filled with water (FIG. 10D), respectively. FIGS. 11C and 11D show representative voltage outputs for the floating and glued piezoelectric gastrointestinal sensors, respectively; both plots show a steady increase as pressure builds up. The associated average pressure values during water infusion follow a similar trend as shown in FIGS. 11E and 11F. Here, the voltage output due to 200 mL water infusion (four individual trials) yielded four consecutive peaks as the water was infused in 50 mL increments into the balloon (FIGS. 11C and 11D).

FIGS. 12A-12C show the initial voltage output (baseline) of a piezoelectric gastrointestinal sensor under different conditions. FIG. 12A shows the baseline voltage with the sensor floating in the balloon. FIG. 12B shows the baseline voltage with the sensor glued to the balloon. And FIG. 12C shows the baseline voltage with the sensor in an ex vivo stomach (described below). Together, these plots show that the initial voltage output (baseline) of a piezoelectric gastrointestinal sensor is relatively constant when the piezoelectric gastrointestinal sensor does not experience any pressure variations.

We observed the baseline voltage due to the external forces, such as gravity and atmospheric pressure that are experienced by the sensors under different conditions. In case I, the piezoelectric gastrointestinal sensor freely floats inside the balloon and undergoes large deformations and out of plane bending by water infusion. The induced deformations and strains generate a significant voltage output in the PZT ribbons comparing to the baseline voltage (see FIGS. 11A and 12A). In case II, however, the device is glued to the balloon wall and its motion is constrained to the in-plane deformations induced by the balloon expansion.

There is a slight curve difference between Case I (free-floating sensor) and Case II (sensor affixed to balloon's inner wall). Case II yields higher voltage output than Case I due to the higher effective in-plane strain built in piezoelectric gastrointestinal sensor glued on the inner wall of the balloon. Additionally, in Case II, given that the latex material of the balloon is significantly softer than the sensor and the glue, the balloon's expansion mainly occurs in the latex section, not on the sensor section. The voltage output generated by water infusion in case II is, hence, not significant comparing to the baseline voltage (see FIGS. 11B and 12B). Since the stomach tissue, which is in contact with the piezoelectric gastrointestinal sensor is mechanically much softer than the device materials, a behavior similar to case II is observed in the ex vivo experiments described below.

Pressure Change in the Balloon

Natural rubber does not deform according to Hooke's Law, thus creating a nonlinear relationship between a latex balloons' volume and internal pressure. Without being bound by any particular theory, the internal pressure of a balloon can be related its radius. This relationship can be expressed as a theoretical pressure curve that increases rapidly to a pronounced peak and then gradually drops to zero as the radius approaches infinity.

The relationship between a balloon's internal pressure and radius can be transformed and used to predict the radius at the maximum internal pressure:

$$r_P = 1.38 r_0, \quad (1)$$

where $r_P$ is the radius at maximum internal pressure and $r_0$ is the uninflated radius. Assuming the balloon is a sphere and measuring the initial volume of the balloon to be 50 mL, the initial radius can be calculated using the formula:

$$V = \frac{4}{3}\pi r^3, \quad (2)$$

where V is the volume and r is the radius. This yields an initial radius of 2.29 cm, which is used as $r_0$ in Eq. 1 to calculate $r_P$ (3.16 cm). The $r_P$ is then used as the radius in Eq. 2 to determine the volume of the balloon at which the internal pressure will be at a maximum (~132 cm³ or 132 mL). Considering the pressure readings from the balloon in FIGS. 11E and 11F, it is reasonable to assume that the maximum pressure in the balloon (Case I and II) occurred between the volume intervals of 100 mL and 150 mL, which correlates with the predicted value. Therefore, the collected balloon pressure readings appear as expected and follow the trend of the theoretical pressure curve.

Finite Element Modeling of the Piezoelectric Gastrointestinal Sensor

Next, we modeled the behavior of the piezoelectric gastrointestinal sensor in case II using finite element (FE) method (ABAQUS/Standard, Simulia, Providence, R.I.) to approximate electrical output as a function of key design parameters, material properties, and applied contractions. The model represented 120 separate piezoelectric ribbons of five different layers (20 nm Ti, 300 nm Pt, 500 nm PZT, 10 nm Cr, and 200 nm Au). The piezoelectric ribbons were mounted on a 75 μm Kapton layer, which was bonded (glued) to a spherical balloon.

The layers of the piezoelectric ribbons were modeled as linear elastic materials with properties shown below in Table 1. The balloon was modeled as a hyperplastic material with μ=0.5 MPa and K=250 MPa, where μ and K are shear and bulk modulus, respectively.

TABLE 1

| Material | Kapton | Ti | Pt | PZT | Au | Cr |
|---|---|---|---|---|---|---|
| Elastic Modulus (GPa) | 2.5 | 116 | 168 | 63 | 78 | 279 |
| Poisson's ratio | 0.34 | 0.32 | 0.38 | 0.3 | 0.44 | 0.21 |

The piezoelectric behavior of the PZT layer was modeled using the built-in piezoelectric material model in ABAQUS (see Dagdeviren, C. et al., "Conformal piezoelectric energy harvesting and storage from motions of the heart, lung, and diaphragm," PNAS 111, 1927-1932 (2014) for values). The overlapping surfaces of different layers were constrained to move with each other using TIE constraints in ABAQUS. The series and parallel electric connections were generated by constraining the electric potential between the different surfaces of the PZT layers. The mechanical behavior of the device was modeled in a Static Step without considering any large deformation (NLGEOM=OFF). The instability of piezoelectric gastrointestinal sensor was modeled using the Buckle Module of ABAQUS. The inflation of the balloon was modeled using Fluid Filling and Fluid Flux options in ABAQUS.

To approximate the electric output of piezoelectric gastrointestinal sensor analytically, we found the strain generated inside the sensor by water infusion. A single layer hyper-elastic balloon experiences equibiaxial stress as:

$$\sigma_\theta = \sigma_\phi = \sigma = \mu\left(\lambda^2 - \frac{1}{\lambda^4}\right) \quad (1)$$

where $\lambda = r/R$ is the principal stretch (R and r are the balloon radius before and after deformation) and μ is the shear modulus of the material. Also, the internal pressure generated by water infusion can be obtained as:

$$P = \frac{2\mu H}{R}\left(\frac{1}{\lambda} - \frac{1}{\lambda^7}\right) \quad (2)$$

If a planar piezoelectric patch is glued to the balloon wall, the balloon deformation pattern in the glued area will change. Particularly, if the patch is circular and much stiffer than the balloon material, we can neglect the deformation of the patch. And if the deformation in the rest of the balloon is not affected by the circular patch, the balloon should remain almost spherical after deformation. Using these simplifications, Equations (1 and 2) are valid for pressure and stresses in the balloon section while the volume of the balloon can be calculated as:

$$V = \frac{\pi r^3}{3}(2 + 2\cos\gamma + \cos\gamma \sin\gamma^2) \quad (3)$$

where $\gamma = \rho/r$. Using these formulas, we can approximate the stresses in the balloon and then transfer the same stresses to the Kapton section and piezoelectric ribbons using the rule of mixture for composite materials. Having the stresses in the piezoelectric ribbons and assuming linear elasticity, strain and electric potential in the system was found using similar formulas suggested in Dagdeviren, C. et al. Conformal piezoelectric energy harvesting and storage from motions of the heart, lung, and diaphragm. *PNAS* 111, 1927-1932 (2014), which is incorporated herein by reference.

FIG. 13A shows the finite element model of the piezoelectric gastrointestinal sensor device attached to a hyperelastic spherical balloon. Both undeformed (black solid line) and inflated (black dash line) stages are shown. The mechanical deformations of the balloon and piezoelectric gastrointestinal sensor are magnified three times.

FIG. 13B shows the simulated strain distribution in piezoelectric gastrointestinal sensor generated by infusing the balloon with 200 mL incompressible fluid in four steps, LE: Max. principle strain. The strain distribution in the ribbon is less than 0.01, which is reported as the failure strain for thin film PZT ribbons. The piezoelectric gastrointestinal sensor device was modeled in an open circuit in FE analysis (the electric circuit cannot be modeled in ABAQUS).

FIGS. 13C-13E are plots obtained from the FE model in an open circuit. FIG. 13C is a plot of the electric potential generated with piezoelectric gastrointestinal sensor. It shows that, for this example, the maximum electric potential generated by the sensor is <40 mV. Because the FE model does not account for the electric circuit, the electric potential does not dissipate during the time. To model the device in an electric circuit, we developed an approximate analytical model of the PZT patch glued to the balloon (see above). As shown in FIG. 13C, the electric potential generated by the device shows four step-like increases corresponding to the four steps of water infusion. Moreover, given that the change in internal pressure generated in the balloon decreases in each step (see FIGS. 11E, 11F and 13E), the mechanical input to the PZT ribbon and the electric potential generated decrease in the successive steps, as can be seen in FIG. 13D.

Ex Vivo Assessment of Electrical Performance

We tested the device performance in the above in vitro setup, by substituting a freshly explanted swine stomach for the balloon, to mimic the in vivo environment. Here, a swine stomach was procured twenty minutes after euthanization from a local slaughterhouse (see below for details). More specifically, a swine esophagus, stomach, and a portion of the small intestine after the duodenum were harvested twenty minutes after euthanization from a local slaughterhouse. The contents were held in a chilled container at approximately 4° C. during its transport. The stomach was then moved to a sterile hood and a dissection was performed. The esophagus was removed from the stomach with medical scissors along the gastro-esophageal junction. The gastric contents were emptied using a 60 mL Monojet oral medication syringe and water in order to remove any particulate that had adhered to the mucosal layer, which could have interfered with adhesion of the device and the experimental readings. The small intestinal tract was then removed after the duodenum by using medical scissors. At no point were any other incisions made in the stomach tissue, ensuring structural and fluidic integrity. After dissection, the stomach was attached at the level of the gastro-esophageal junction to the experimental setup. The stomach was ligated at the level of the duodenal bulb to prevent leakage of fluids during the experiments.

(On another occasion, a similar dissection occurred including the removal of the esophagus at the gastro-esophageal junction and the small intestine after the duodenum. In this instance, the stomach tissue was extracted in 2 cm×2 cm sections (e.g., as in FIG. 6B) leaving all tissue layers intact in order to test adhesion of the device to the mucosal layer. The extracted tissue was placed in a solution of Gibco® 1× Dulbecco's phosphate-buffered saline (DPBS) and stored at 4° C. until testing occurred.)

FIGS. 14A and 14B are photographs of an ex-vivo stomach integrated with in vitro set-up before and after 200 mL water infusion, respectively. FIG. 14C is a plot of voltage versus time graph for a piezoelectric gastrointestinal sensor in the ex vivo stomach during the 200 mL water infusion in 50 mL increments. FIG. 14D is a plot of the representative voltage output versus time graph for every 50 mL water infusion for piezoelectric gastrointestinal sensor in the ex vivo stomach. FIG. 14E is a graph of average pressure variation during the water infusion in FIGS. 14C and 14D for piezoelectric gastrointestinal sensor in the ex vivo stomach. The error bars in FIG. 14E are the standard deviation with center values as mean. The collective results confirm that the water infusion in general, increases the pressure buildup inside the stomach, until a maximum is reached. Thus, the created in-plane strain within the piezoelectric layer of piezoelectric gastrointestinal sensor, due to the gastrointestinal pressure, was transformed as a voltage output.

Given that latex has an elastic modulus of 1.5 MPa and the measured un-stretched volume of a latex balloon is 50 mL, consistent initial pressure readings with instilled water volumes were observed. On the other hand, the swine stomach had a resting un-stretched volume of approximately 1-2 L and the measured swine gastric mucosa yielded an elastic modulus of 0.7 MPa±0.1 as shown in FIG. 15. This large difference in volume between the balloon and stomach, while still infusing the same amount of water, allowed the balloon to reach a maximum internal pressure during testing, but not the stomach. The increasing nature of the relationship between the stomach's volume and pressure is, therefore, comparable to only the initial segment of the curve describing the balloons relationship between its volume and internal pressure, before the maximum is reached.

With the latex balloons being about twice as stiff and having a significantly smaller initial volume than the stomach, higher pressures were anticipated in comparison to the ex vivo stomach. This was supported by the observation that pressure values from the stomach were an order of magnitude below that of the latex balloon. Even with the disparity in pressure readings of in vitro and ex vivo experiments, the voltage outputs from both arrangements exhibited comparable values and similar positive trends with respect to the volume of water infused.

In Vivo Assessment in a Yorkshire Swine Model

We further confirmed the functionality of piezoelectric gastrointestinal sensor in a swine large animal model. Two Yorkshire swine ~45 kg in weight were briefly sedated, intubated, and maintained on isoflurane. Randomization of animals was not performed. The morning feed was held on the day of the procedure and the animals sedated with Telazol (tiletamine/zolazepam) 5 mg/kg, xylazine 2 cmg/kg, atropine 0.04 mg/kg. To confirm gastric deployment of the piezoelectric gastrointestinal sensor system an esophageal overtube (US Endoscopy) was placed in the esophagus and the gastric cavity was accessed endoscopically. Air was instilled with the aid of a Pentax EPK-I Endoscopy Processor and water instilled into the stomach through the access port in the endoscope.

Endoscopic Insertion and Adhesion Test

To place the piezoelectric gastrointestinal sensor in the gastric cavity endoscopically, we folded the flexible device in a dissolvable gelatin capsule as shown in FIG. 16A. The timescales of gelatin capsule dissolution, device unfolding, and settling on stomach lining are ~5 minutes, ~10 seconds, and ~5 seconds, respectively, as shown in the series of photographs in FIG. 16B.

The sensor's adhesion strength was measured using a digital force meter (Mark-10, USA), according to the following procedure: the stomach was secured, and the sensor substrate was connected to a force meter. The piezoelectric gastrointestinal sensor was peeled away at a maximum speed of 1,000 mm/min in an upward direction, parallel to the width of the sensor, at room temperature. The maximum value of the force during this process defined the adhesion force. A piezoelectric gastrointestinal sensor with a 75 μm thick polyimide substrate and lateral dimensions of 2.5 cm (length)×2 cm (width) showed an average adhesion force of 0.064 N. The detachment of the piezoelectric gastrointestinal sensor from the stomach lining during the application with an average adhesion force of 0.064 N is unlikely because the piezoelectric gastrointestinal sensor has intimate integration on the stomach lining as shown in FIG. 16B.

Since the sensor compensated for the applied compression via out-of-plane bending with a maximum strain of $\varepsilon = 4 \times 10^{-3}$ in the ribbons, folding the sensor did not induce any mechanical and electrical problem. As the capsule dissolved in GI fluid, the piezoelectric gastrointestinal sensor naturally unfolded as shown in FIG. 16B and settled intimately onto the stomach lining as shown in FIG. 16C.

Distinguishing Air Insufflation from Liquid Ingestion

FIGS. 17A-17D illustrate serial air and water instilments performed to mimic gastric expansion secondary to ingestion. FIGS. 17A and 17B show the piezoelectric gastrointestinal sensor on the wall of stomach during inflation and deflation, respectively. FIG. 17C shows sensor voltage data collected during these treatments. In the in vivo experiments, the baseline voltage was also observed since the pressure values are influenced by not only external forces, but also internal forces, such as those from muscles and fluids.

FIG. 17D shows a representative voltage output versus time graph of a cycle of air inflation and deflation. When air was introduced into the stomach, the piezoelectric gastrointestinal sensor experienced a sudden pressure change that resulted in a significant voltage increase from ~10 mV to 60 mV. Over a course of 40 seconds of inflation, the inner pressure stabilized and resulted in a plateau voltage curve, whereas a substantial decrease in voltage from ~40 mV to the base state occurred as the air was released. Here, the potential to sense changes associated with air ingestion have the capacity to guide evaluation and treatment in cases of aerophagia or significant small intestine bacterial overgrowth (SIBO) as well as disacharidase deficiencies where excess gas can manifest in pain.

FIG. 18A shows data from a second experiment conducted by instilling 200 mL water in 50 mL increments (four separate trials) into the stomach and recording the voltage output from the piezoelectric gastrointestinal sensor. The traces in FIG. 18A, which are for infusion of water, not air, have a different shape than the traces in FIG. 17C for air insufflation/deflation. This indicates that voltage readings from the sensor can be used to distinguish between air insufflation and liquid ingestion.

FIG. 18B shows a representative voltage output versus time of a cycle of water infusion and suction. The 200 mL water intake into the stomach resulted in an increase of the voltage output from ~8 mV to 30 mV incrementally with respect to a repetitive 50 mL water infusion. As in the deflation case, a substantial decrease in voltage from ~30 mV to ~15 mV was observed due to the water outlet. The initial voltage output (baseline) of a piezoelectric gastrointestinal sensor yields a constant line as in the in vivo and ex vivo tests because there is no pressure variation. Here, the voltage does not return to the initial state because of the remaining water inside the stomach. The capacity to sense fluids, raises the potential of sensing general foodstuffs, which could add a new mode of evaluation of patients suffering from obesity.

Simulated Walking and Energy Harvesting

Next, we simulated walking animal activity that could potentially be used to harvest mechanical energy from GI motility by applying lateral motions (LM) and abdominal palpations (palp) directly on the stomach of a sedated animal as shown in FIGS. 19A and 19B. The output voltage recorded during abdominal palpation demonstrates the ability to sense gastrointestinal motility due to food ingestion and the potential functionality to simultaneously generate electrical power. Associated output voltage during the LM and resting cycles and abdominal palpation on the stomach of the swine to simulate the stomach movement are summarized in FIGS. 19C and 19D. FIG. 19C shows a periodic voltage output, which is consistent with the LM-resting cycle. The voltage output is, however, slightly (~10 mV) low when abdominal palpation is applied, as shown in FIG. 19D. Additional trials can be seen in FIGS. 19E and 19F.

In Vivo Ingestion Motility Evaluation in Yorkshire Swine Model

Furthermore, to validate the in vivo capacity for motility monitoring we conducted experiments in awake and ambulating Yorkshire swine. Specifically, the piezoelectric gastrointestinal sensor was placed in the gastric cavity of a ~50 kg female Yorkshire swine. The pig was anesthetized with tiletamine/zolazepem, xylazine and atropine (4 mg/kg, 2 mg/kg, 0.04 mg/kg, respectively via intramuscular administration), then intubated and maintained on 2-3% isoflurane in oxygen. Lidocaine (1%) was administered locally and a 20 French percutaneous endoscopic gastrostomy (PEG) tube (Halyard Health MIC Kit, 7160-20)) was placed on the left craniolateral aspect of the abdomen.

Using endoscopic guidance and an overtube, the piezoelectric gastrointestinal sensor attached to electronic connection wires was passed into the stomach and the electronic connection wires were externalized through a percutaneous gastrostomy (PEG) tube as shown in FIG. 20A. The PEG tube and wires were secured using a bandage. Positioning was confirmed endoscopically and radiographically as shown in FIGS. 20B and 20C. The animal recovered well, and recordings were obtained while the animal ambulated and ingested food. The animal was maintained on a liberal diet.

Repeated measurements in the awake and ambulating pig were performed twice a day, 24 and 48 hours after placement of the device. The voltage outputs were collected while the animal ambulated and during milk ingestion. The corresponding voltage output graphs for morning (FIGS. 20D and 20F) and afternoon (FIGS. 20E and 20G) trials of before and after milk ingestion during Day #1 and Day #2, demonstrated consistent voltage increases during ingestion. The sensor performed in an awake and ambulating large animal and remained fully functional following exposure to the gastric environment for 48 hours.

These experimental results show that the piezoelectric gastrointestinal sensor exhibits mechanical and electrical robustness that enables stable operation inside the gastric cavity, while providing a consistent and relevant evaluation of the motility states of the stomach. Additionally, these experimental results show that the sensor can use energy harvesting to serve as a self-powered system that is more compatible with ingestion.

Notes on Experimental Methods

All procedures were conducted in accordance with protocols approved by the Massachusetts Institute of Technology Committee on Animal Care.

Tissue Harvesting

A swine GI tract was collected from Lemay & Sons Beef LLC in Goffstown, N.H. The tissue was transported in a cooler and when it arrived at MIT, placed on ice and transferred in a laminar flow hood for dissection. The stomach was dissected from the gastroesophageal junction and from the duodenum in order to separate the stomach from the GI tract. An incision was made in the anterior wall where a section of stomach was removed (epithelial and muscle layers intact). From there, the epithelial layer was detached from the muscle layer by carefully cutting the loose connective tissue using scissors. The new sections were cut into approximately 23.5 mm×60 mm pieces.

Tissue Characterization

The newly sectioned samples were tested in tension on an Instron 5943 running Bluehill 3 software. Specially designed grip faces were fabricated in order to test the tissue samples in screw-action grips, to avoid tissue slippage. The samples were placed in between the grip faces and clamped down leaving a gauge length of 17.5 mm for testing. The test ran at an extension rate of 0.05 mm/s. The samples were pulled until failure. The entirety of this experiment, from harvesting to tissue failure, was approximately 5-6 hours. The data from the tensile testing of sections of the epithelial layer was used for analysis.

Raw data was taken from the Instron and plotted to show stress as a function of strain. Because of tissue's poroelastic nature, only the initial phase of the stress-strain curve can be utilized to determine elastic moduli. Therefore, the data was truncated to a strain range of 0.4 to 0.45 to capture a linear portion within this initial phase. The elastic modulus was determined for each tissue sample individually by calculating the ratio of the increments of tensile stress to the increments of strain. These values were used to calculate the average and standard deviation of the elastic modulus of swine epithelial tissue. FIG. 15 shows the truncated stress-strain curve of the swine gastric mucosa samples.

Cell Culture Study

HT-29-MTX-E12 cells were purchased from the European Collection of Authenticated Cell Cultures, Operated by Public Health England. HeLa cells were purchased from ATCC®. Both were cultured in DMEM High glucose pyruvate (11995-065), 10% FBS (heat inactivated) (Lifetechnologies, Cat #10082-147), 1% Gibco MEM Non-Essential Amino Acid Solution (Lifetechnologies, Cat #11140-050) and 1% Pen/Strep (Lifetechnologies, Cat #15140122) under standard cell culture conditions (37° C., 5% CO2). C2BBe1 were purchased from ATCC® and cultured in DMEM High glucose pyruvate (11995-065), 10% FBS (heat inactivated) (Lifetechnologies, Cat #10082-147), Human Transferrin-Insulin-Selenium (ITS-G) 100× (Lifetechnologies, Cat #41400-045) and 1% Pen/Strep (Lifetechnologies, Cat #15140122) under standard cell culture conditions (37° C., 5% CO2). For experiments, cells were detached by using 0.25% (v/v) Trypsin-EDTA solution (Invitrogen). All cells tested negative for *mycoplasma* contamination.

Immunohistochemical Staining

Cell samples were fixed with 4% (v/w) formalin in PBS for 30 minutes at room temperature, washed with PBS, permeabilised with 0.25% (v/v) Triton-X-100/PBS for 2 minutes, washed with PBS and then blocked with 4% (w/v) bovine serum albumin in PBS for 1 hour. Then the samples were stained with Actingreen™ 488 ReadyProbes® Reagent for 40 minutes followed by DAPI (4',6-Diamidino-2-Phenylindole, Dihydrochloride) for 10 minutes (both purchased from Lifetechnologies). The samples were washed three times and then mounted on a cover slide using ProLong® Diamond Antifade Mountant (Thermo Fisher Scientific).

CONCLUSION

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize or be able to ascertain, using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. A device for sensing deformation of a gastrointestinal tract of a mammal, the device comprising:
   a flexible substrate, wherein the flexible substrate is rollable in a first direction;
   a set of piezoelectric elements with each piezoelectric element in the set of piezoelectric elements having a length along the first direction that is greater than a width of that piezoelectric element, disposed as groups of piezoelectric elements on the flexible substrate, to produce an electrical signal in response to the deformation of the gastrointestinal tract of the mammal, wherein piezoelectric elements within a group of piezoelectric elements are electrically connected in parallel, and wherein the groups of piezoelectric elements are electrically connected in series;
   a polymer layer, disposed on the set of piezoelectric elements, to insulate electrodes of the set of piezoelectric elements; and
   a biocompatible sealant, disposed on the polymer layer and the set of piezoelectric elements on the flexible substrate, to protect the set of piezoelectric elements from acid in the gastrointestinal tract, wherein the biocompatible sealant has a Young's modulus of 0.01 GPa to 5.0 GPa.

2. The device of claim 1, wherein the flexible substrate is rolled and encapsulated in a dissolvable capsule and configured to unroll in response to the dissolvable capsule dissolving.

3. The device of claim 2, wherein the dissolvable capsule is configured to be endoscopically inserted within the gastrointestinal tract of the mammal.

4. The device of claim 1, wherein each piezoelectric element of the set of piezoelectric elements comprises a biocompatible piezoelectric material.

5. The device of claim 1, wherein the biocompatible sealant comprises curable epoxy.

6. The device of claim 1, wherein the biocompatible sealant has a thickness of about 100 nm to about 10 microns.

7. The device of claim 1, further comprising:
   a wireless transmitter, operably coupled to the set of piezoelectric elements, to transmit the electrical signal to a receiver outside of the mammal.

8. The device of claim 7, wherein the set of piezoelectric elements is configured to power the wireless transmitter with energy harvested from the gastrointestinal tract.

9. A device for producing an electrical signal in response to expansion and/or contraction of a lumen wall of a gastrointestinal tract of a mammal, the device comprising:
   a flexible substrate;
   an array of biocompatible piezoelectric elements, disposed on the substrate, to produce the electrical signal in response to the expansion and/or contraction of the lumen wall of the gastrointestinal tract of the mammal;
   a polymer, encapsulating the array of biocompatible piezoelectric elements, to insulate electrodes attached to the array of biocompatible piezoelectric elements; and
   a biocompatible sealant, disposed on the polymer, to protect the array of biocompatible piezoelectric elements and the polymer from acid in the gastrointestinal tract, such that when the device undergoes deformation during use, the device undergoes out-of-plane bending and an in-plane bending strain experienced by each piezoelectric element of the array of piezoelectric elements is lower than a failure strain of that piezoelectric element, wherein the device is rolled and encapsulated in a dissolvable capsule and configured to unroll when the dissolvable capsule dissolves.

10. The device of claim 9, wherein the biocompatible sealant is configured to protect the array of biocompatible piezoelectric elements and the polymer from acid in the gastrointestinal tract for at least 48 hours.

11. The device of claim 9, wherein the biocompatible sealant has a thickness of about 100 nm to about 10 microns.

12. The device of claim 9, wherein the biocompatible sealant has a Young's modulus of 0.01 GPa to 5.0 GPa.

13. The device of claim 9, wherein the device is configured to measure at least 10,000 expansions and/or contractions of the lumen wall.

14. The device of claim 9, wherein the array of biocompatible piezoelectric elements includes at least two rows of biocompatible piezoelectric elements and at least two columns of biocompatible piezoelectric elements.

15. A method comprising:
inserting a device into the gastrointestinal tract of a mammal, the device comprising a piezoelectric element disposed on a flexible substrate, the flexible substrate being rolled and encapsulated in a dissolvable capsule; and
allowing the dissolvable capsule to dissolve within the gastrointestinal tract so as to cause the flexible substrate to unroll within the gastrointestinal tract and to adhere to a lumen wall of the gastrointestinal tract,
such that upon deformation after adhering to the lumen wall, the device undergoes out-of-plane bending and an in-plane bending strain experienced by the piezoelectric element during said out-of-plane bending is lower than a failure strain of the piezoelectric element.

16. The method of claim 15, wherein inserting the device comprises endoscopically inserting the device into the gastrointestinal tract of a mammal.

17. The method of claim 15, further comprising:
sensing deformation of the lumen wall of the gastrointestinal tract with the device for about 12 hours to about 48 hours.

18. The method of claim 15, further comprising:
sensing deformation of the lumen wall of the gastrointestinal tract with the device for at least about 48 hours.

19. The method of claim 15, further comprising:
sensing deformation of the lumen wall of the gastrointestinal tract with the device for at least about 36 hours.

20. The method of claim 15, further comprising:
sensing deformation of the lumen wall of the gastrointestinal tract with the device for at least about 24 hours.

21. The method of claim 15, further comprising:
sensing deformation of the lumen wall of the gastrointestinal tract with the device for at least about 12 hours.

22. The method of claim 21, wherein sensing the deformation of the lumen wall comprises generating an electrical signal with the piezoelectric element.

23. The method of claim 21, further comprising:
wirelessly transmitting a signal representing the deformation of the lumen wall to a receiver outside the mammal with a transmitter powered by the piezoelectric element.

24. The method of claim 21, further comprising:
determining that the mammal has ingested a fluid based on the deformation of the lumen wall.

25. The method of claim 15, further comprising:
sensing at least 10,000 expansions and/or contractions of the lumen wall of the gastrointestinal tract with the device.

26. A method comprising:
sensing expansion and/or contraction of a lumen wall of a gastrointestinal tract of a mammal with a device disposed on the lumen wall, the device comprising:
a film-like flexible substrate, wherein the film-like flexible substrate is rollable in a first direction;
a set of piezoelectric elements with each piezoelectric element in the set of piezoelectric elements having a length along the first direction that is greater than a width of that piezoelectric element, the set of piezoelectric elements disposed on the film-like flexible substrate as an array of groups of piezoelectric elements, wherein piezoelectric elements within a group of piezoelectric elements are electrically connected in parallel, and wherein the groups of piezoelectric elements are electrically connected in series;
a layer of polymer disposed on the set of piezoelectric elements; and
a layer of sealant disposed on the layer of polymer, wherein the layer of sealant has a Young's modulus of 0.01 GPa to 5.0 GPa, and wherein the layer of sealant encapsulates the entire device except one side of the substrate that couples to the lumen wall.

* * * * *